(12) United States Patent
Antunes et al.

(10) Patent No.: US 11,478,200 B2
(45) Date of Patent: Oct. 25, 2022

(54) BLOOD PRESSURE AND AUTOREGULATION MONITORING

(71) Applicant: Covidien LP, Mansfield, MA (US)

(72) Inventors: Andre Antunes, Edinburgh (GB); Paul S. Addison, Edinburgh (GB); Dean Montgomery, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 987 days.

(21) Appl. No.: 16/218,160

(22) Filed: Dec. 12, 2018

(65) Prior Publication Data

US 2020/0187866 A1    Jun. 18, 2020

(51) Int. Cl.
*A61B 5/00* (2006.01)
*A61B 5/021* (2006.01)

(52) U.S. Cl.
CPC ............ *A61B 5/7278* (2013.01); *A61B 5/021* (2013.01); *A61B 5/7203* (2013.01); *A61B 5/7257* (2013.01)

(58) Field of Classification Search
CPC ..... A61B 5/7278; A61B 5/021; A61B 5/7203; A61B 5/7257; A61B 5/7221; A61B 5/02028
See application file for complete search history.

(56) References Cited

U.S. PATENT DOCUMENTS

| | | | |
|---|---|---|---|
| 5,743,267 A | 4/1998 | Nikolic et al. | |
| 6,599,251 B2 | 7/2003 | Chen et al. | |
| 6,689,069 B2 | 2/2004 | Bratteli et al. | |
| 7,070,566 B2 | 7/2006 | Medero et al. | |
| 7,927,283 B2 | 4/2011 | Riobo Aboy | |
| 8,366,627 B2 | 2/2013 | Kashif et al. | |
| 8,702,604 B2 | 4/2014 | Karamanoglu et al. | |
| 9,474,451 B2 | 10/2016 | Brady et al. | |
| 9,861,317 B2 | 1/2018 | Ochs | |
| 2009/0326386 A1 | 12/2009 | Sethi et al. | |

(Continued)

FOREIGN PATENT DOCUMENTS

WO    2017001023 A1    1/2017

OTHER PUBLICATIONS

Chuan et al., "Is Cerebrovascular Autoregulation Associated with Outcomes After Major Noncardiac Surgery? A Prospective Observational Pilot Study," Acta Anaesthesiologica Scandinavica, Jul. 11, 2018, 10 pp.

(Continued)

*Primary Examiner* — Manuel L Barbee
(74) *Attorney, Agent, or Firm* — Shumaker & Sieffert, P.A.

(57) ABSTRACT

In some examples, a method includes receiving a signal indicative of a blood pressure of a patient and identifying at least one first portion of the signal comprising a first characteristic of the signal exceeding a first threshold. The method also includes identifying at least one first portion of the signal comprising a second characteristic of the signal exceeding a second threshold, the first characteristic being different than the second characteristic. The method further includes determining a filtered signal indicative of the blood pressure of the patient by excluding the at least one first portion and the at least one second portion from the signal. The method includes determining a set of mean arterial pressure values based on the filtered signal and determining an autoregulation status of the patient based on the set of mean arterial pressure values.

20 Claims, 14 Drawing Sheets

(56) References Cited

U.S. PATENT DOCUMENTS

| | | |
|---|---|---|
| 2011/0105912 A1 | 5/2011 | Widman et al. |
| 2012/0197139 A1* | 8/2012 | Lee ................. A61B 5/742 600/494 |
| 2015/0327779 A1* | 11/2015 | Breskin ............ A61B 8/0808 600/407 |
| 2016/0367197 A1 | 12/2016 | Addison et al. |
| 2017/0095161 A1 | 4/2017 | Addison et al. |
| 2017/0105631 A1 | 4/2017 | Addison et al. |
| 2017/0105671 A1 | 4/2017 | Borgos |
| 2017/0181649 A1* | 6/2017 | Carter ............. A61B 5/02416 |
| 2018/0014791 A1 | 1/2018 | Montgomery et al. |
| 2018/0020991 A1 | 1/2018 | Aung et al. |
| 2018/0049649 A1 | 2/2018 | Addison et al. |
| 2018/0249916 A1 | 9/2018 | Bienek et al. |
| 2018/0333055 A1* | 11/2018 | Lamego ............. A61B 5/0235 |
| 2018/0338731 A1 | 11/2018 | Addison et al. |

OTHER PUBLICATIONS

Tsalach et al., "Cerebral Autoregulation Real-Time Monitoring," PLoS ONE vol. 11, No. 8, Aug. 29, 2016, 14 pp.
Scheeren et al., "Journal of clinical monitoring and computing 2016 end of year summary: monitoring cerebral oxygenation and autoregulation," Journal of Clinical Monitoring and Computing, vol. 31, No. 2, Apr. 2017, 6 pp.
U.S. Appl. No. 15/962,486, filed Apr. 25, 2018, by Montgomery.
U.S. Appl. No. 16/184,638, filed Nov. 8, 2018, by Addison.
U.S. Appl. No. 16/169,794, filed Oct. 24, 2018, by Montgomery.

\* cited by examiner

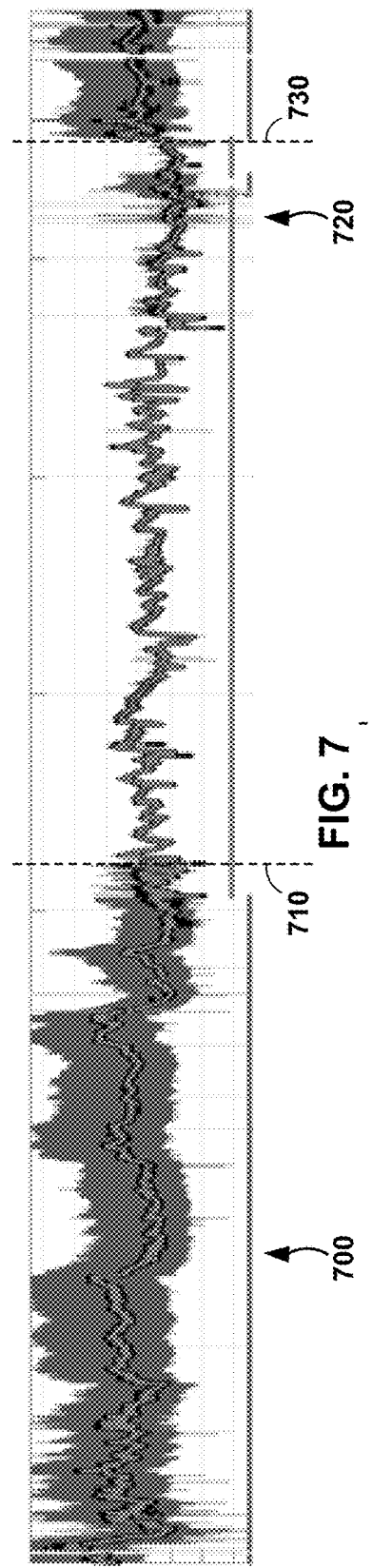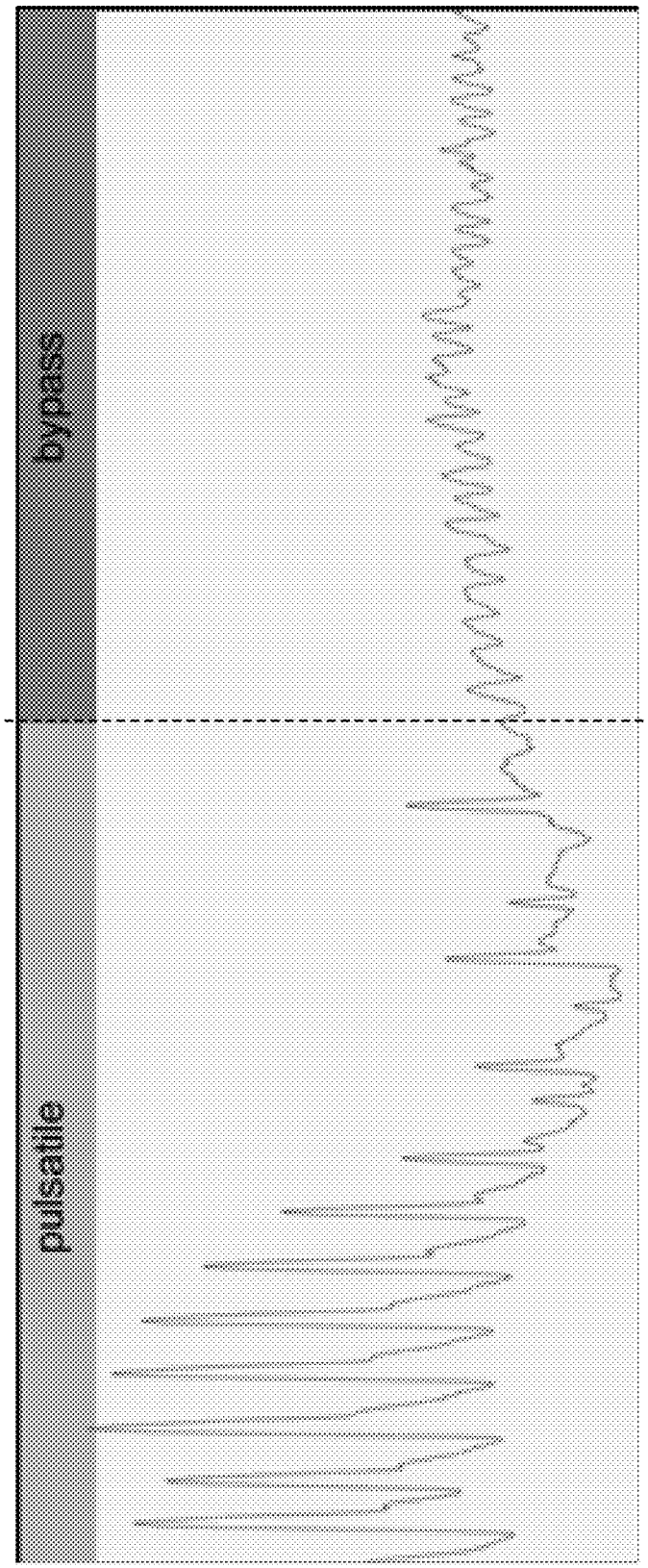
FIG. 7
FIG. 8

BLOOD PRESSURE AND AUTOREGULATION MONITORING

TECHNICAL FIELD

This disclosure relates to physiological parameter monitoring.

BACKGROUND

Cerebral autoregulation (CA) is the response mechanism by which an organism regulates cerebral blood flow over a wide range of systemic blood pressure changes through complex myogenic, neurogenic, and metabolic mechanisms. Autoregulation dysfunction may result from a number of causes including, stroke, traumatic brain injury, brain lesions, brain asphyxia, or infections of the central nervous system. Intact cerebral autoregulation function occurs over a range of blood pressures defined between a lower limit of autoregulation (LLA) and an upper limit of autoregulation (ULA).

A physiological monitoring device can determine the autoregulation status of a patient based on the mean arterial blood pressure (MAP) of the patient. The device can determine the MAP as the average of the arterial blood pressure over a cardiac cycle. MAP can be used as an indicator of perfusion, and blood pressures are commonly managed by clinicians in the operating room.

As the left ventricle contracts to push blood into the aorta and arterial system, arterial pressure increases until it reaches its maximum, known as the systolic pressure, before decreasing during the diastole until it reaches minimum pressure, known as the diastolic pressure, thus completing a cardiac cycle. Arterial blood pressure is dependent on the cardiac output from the heart and on the resistance of the cardiovascular system. The exact MAP value depends on a number of factors, such as the heart rate and shape of the pulse.

SUMMARY

This disclosure describes devices, systems, and techniques for determining mean arterial pressure values in the context of autoregulation monitoring. An example device of this disclosure includes processing circuitry configured to receive a signal indicative of a blood pressure of a patient and determine the mean arterial pressure values based on the signal. In some examples, the processing circuitry is configured to identify a portion of the signal comprising one or more characteristics that exceed a respective threshold. The processing circuitry may then exclude or modify the identified portion of the signal to determine a filtered signal. The processing circuitry may then determine the mean arterial pressure values based on the filtered signal.

In some examples, a device includes processing circuitry configured to receive a signal indicative of a blood pressure of the patient and identify at least one first portion of the signal comprising a first characteristic of the signal exceeding a first threshold. The processing circuitry is also configured to identify at least one second portion of the signal comprising a second characteristic of the signal exceeding a second threshold, the first characteristic being different than the second characteristic. The processing circuitry is further configured to determine a filtered signal indicative of the blood pressure of the patient by excluding the at least one first portion and the at least one second portion from the signal. The processing circuitry is configured to determine a set of mean arterial pressure values based on the filtered signal and determine an autoregulation status of the patient based on the set of mean arterial pressure values.

In some examples, a method includes receiving, by processing circuitry, a signal indicative of a blood pressure of a patient and identifying, by processing circuitry, at least one first portion of the signal comprising a first characteristic of the signal exceeding a first threshold. The method also includes identifying, by processing circuitry, at least one first portion of the signal comprising a second characteristic of the signal exceeding a second threshold, the first characteristic being different than the second characteristic. The method further includes determining, by the processing circuitry, a filtered signal indicative of the blood pressure of the patient by excluding the at least one first portion and the at least one second portion from the signal. The method includes determining, by processing circuitry, a set of mean arterial pressure values based on the filtered signal and determining, by processing circuitry, an autoregulation status of the patient based on the set of mean arterial pressure values.

In some examples, a device includes a display, sensing circuitry configured to generate a signal indicative of the blood pressure of the patient, and a memory configured to store a first threshold for a first characteristic of the signal and a second threshold for a second characteristic of the signal. The device also includes processing circuitry configured to identify at least one first portion of the signal comprising the first characteristic of the signal exceeding the first threshold. The processing circuitry is also configured to identify at least one second portion of the signal comprising the second characteristic of the signal exceeding the second threshold, the first characteristic being different than the second characteristic. The processing circuitry is further configured to determine a filtered signal indicative of the blood pressure of the patient by excluding the at least one first portion and the at least one second portion from the signal. The processing circuitry is configured to determine a set of mean arterial pressure values based on the filtered signal and determine an autoregulation status of the patient based on the set of mean arterial pressure values.

In some examples, a device includes a computer-readable medium having executable instructions stored thereon, configured to be executable by processing circuitry for causing the processing circuitry to receive a signal indicative of a blood pressure of the patient and identify at least one first portion of the signal comprising a first characteristic of the signal exceeding a first threshold. The instructions further cause the processing circuitry to identify at least one second portion of the signal comprising a second characteristic of the signal exceeding a second threshold, the first characteristic being different than the second characteristic. The instructions also cause the processing circuitry to determine a filtered signal indicative of the blood pressure of the patient by excluding the at least one first portion and the at least one second portion from the signal. The instructions also cause the processing circuitry to determine a set of mean arterial pressure values based on the filtered signal and determine an autoregulation status of the patient based on the set of mean arterial pressure values.

In some examples, a method includes receiving, by processing circuitry, a signal indicative of a blood pressure of a patient and identifying, by processing circuitry, at least one first portion of the signal comprising a first characteristic of the signal exceeding a first threshold. The method also includes identifying, by processing circuitry, at least one first portion of the signal comprising a second characteristic of the signal exceeding a second threshold, the first characteristic being different than the second characteristic. The method further includes determining, by the processing circuitry, a filtered signal indicative of the blood pressure of the patient by modifying the at least one first portion and the at least one second portion from the signal. The method includes determining, by processing circuitry, a set of mean arterial pressure values based on the filtered signal and determining, by processing circuitry, an autoregulation status of the patient based on the set of mean arterial pressure values.

In some examples, a method includes receiving, by processing circuitry, a signal indicative of a blood pressure of a patient and identifying, by processing circuitry, at least one portion of the signal comprising a characteristic of the signal indicating that the patient is undergoing a cardiopulmonary bypass procedure. The method further includes determining, by the processing circuitry, a set of mean arterial pressure values based on the signal and determining, by processing circuitry, a subset of the set of mean arterial pressure values for the at least one portion of the signal based on a moving average of the signal in response to determining that the characteristic of the signal indicates that the patient is undergoing the cardiopulmonary bypass procedure. The method includes determining, by processing circuitry, an autoregulation status of the patient based on the set of mean arterial pressure values and the subset of the set of mean arterial pressure values for the at least one portion of the signal.

In some examples, a method includes receiving, by processing circuitry, a signal indicative of a blood pressure of a patient and convolving, by processing circuitry, a kernel and blood pressure values of the signal. The method also includes determining, by processing circuitry, signal peaks based on convolving the kernel and the blood pressure values of the signal. The method further includes determining, by the processing circuitry, a set of mean arterial pressure values based on the blood pressure values of the signal and the signal peaks. The method includes determining, by processing circuitry, an autoregulation status of the patient based on the set of mean arterial pressure values.

The details of one or more examples are set forth in the accompanying drawings and the description below. Other features, objects, and advantages will be apparent from the description and drawings, and from the claims.

BRIEF DESCRIPTION OF DRAWINGS

FIGS. 4, 5, 6, 7, and 8 are example graphs showing bypass and pulsatile (e.g., non-bypass) signals.

DETAILED DESCRIPTION

Figure 1:
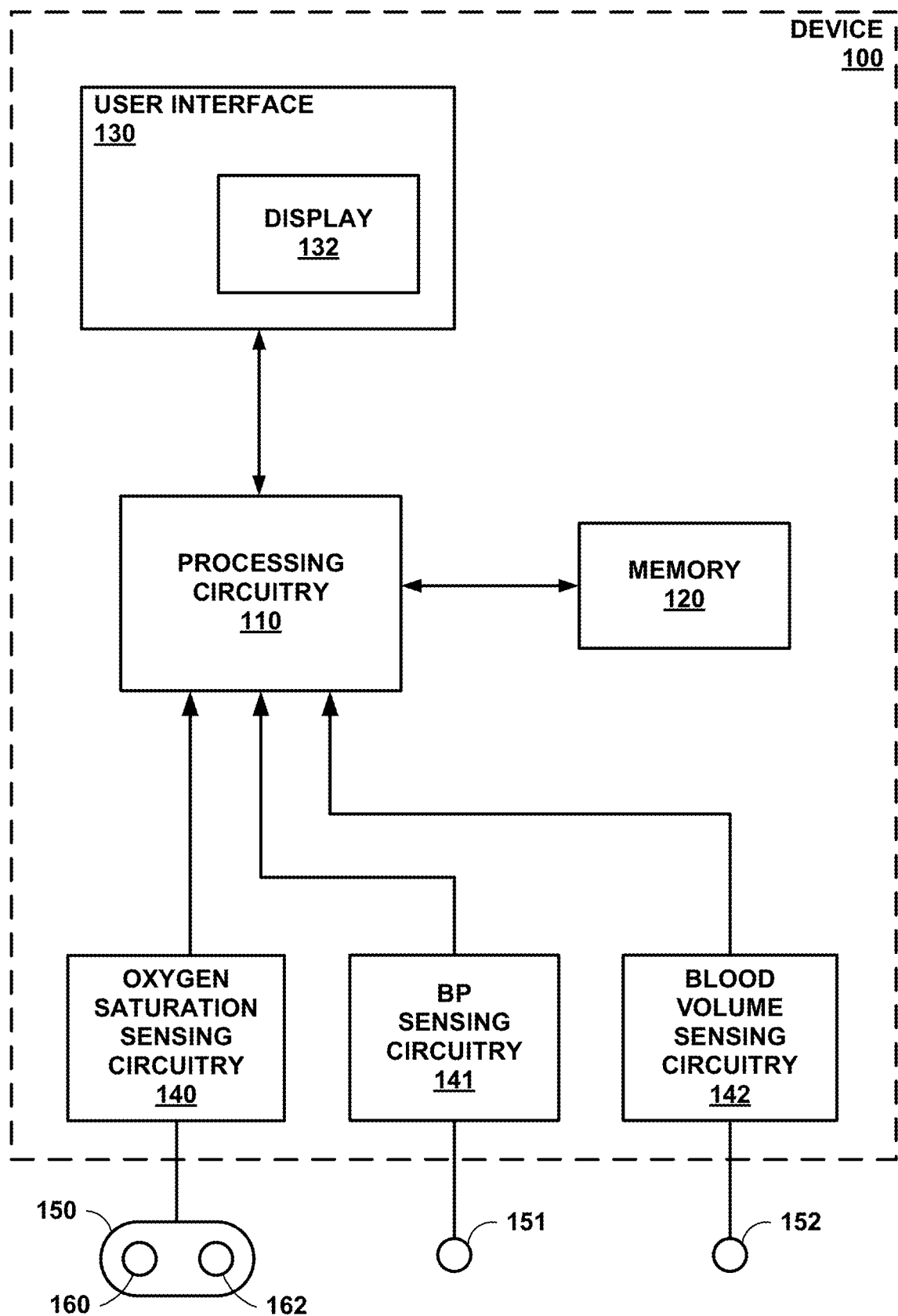
FIG. 1 is a conceptual block diagram illustrating an example device.

This disclosure describes devices, systems, and techniques for determining a set of mean arterial pressure values based on a signal indicative of a blood pressure of a patient. An arterial blood pressure signal, which can be measured invasively or non-invasively, can be affected by several types of conditions which may manifest as artifacts. These artifacts in the blood pressure signal may cause processing circuitry of a system to determine that the blood pressure signal is not valid. Examples of such conditions that may cause artifacts include arterial-line flushing, probe movements, and electrocautery. In other examples, a blood pressure monitoring device may not take into account these artifacts and may only display the current blood pressure information, even if the blood pressure information is contaminated by these artifacts or other undesired noise. During clinical practice, a clinician may expect that the displayed blood pressure will be inaccurate during these times, for example, when the arterial line is being flushed. In such circumstances, the clinician may simply ignore the readings taken from the blood pressure monitor and wait until a reasonable figure comes back on the display. However, these lapses in accurate blood pressures may prevent the clinician or a medical device that uses the blood pressure values from appropriately monitoring the patient's blood pressure during these times.

Cardiac surgery patients often present extremely abnormal beat morphologies that can present a challenge to the monitoring of mean arterial pressure. The monitoring of mean arterial pressure can be difficult when presented with complex pulse morphologies. In addition, the determination of the autoregulation status may be based on the trends of the arterial blood pressure signal, but some blood pressure devices do not process artifacts that affect the trending information that is used for determining autoregulation status. In addition, existing blood pressure devices are not able to classify a portion of the blood pressure signal as pulsatile or as indicating a cardiopulmonary bypass procedure.

The techniques of this disclosure may be able to identify, improve, correct, and/or exclude portions of a blood pressure signal that are affected by conditions that cause artifacts such as line flushing, catheter adjustments, severe noise due to electrocautery, and/or alternating-current (AC) interference. In this manner, processing circuitry may be configured to generate a filtered version of the blood pressure signal to reduce the impact of these conditions to the displayed or otherwise utilized blood pressure signal. In some examples, the processing circuitry may be configured to continue determining mean arterial pressure values during a bypass procedure where there is no cardiac pulse in the blood pressure signal. Other physiological monitoring devices without such bypass detecting techniques may not be capable of providing blood pressures during bypass periods. In contrast, a device of this disclosure may be used in the cardiovascular operating room and other applications and may be able to provide more accurate mean arterial pressure values for both bypass and non-bypass periods.

For example, processing circuitry of a blood pressure device may be configured to identify a portion of the signal including a characteristic exceeding a threshold and determine the filtered signal by excluding or modifying the identified portion of the signal. The processing circuitry can determine the set of mean arterial pressure values based on a filtered version of the signal.

Additionally or alternatively, the processing circuitry may be configured to identify a portion of the signal including a characteristic indicating that the patient is undergoing a cardiopulmonary bypass procedure. The processing circuitry may be configured to identify the portion at least in part by determining that the portion does not satisfy two or more non-bypass conditions. In response to identifying the portion, the processing circuitry can determine mean arterial pressure values for the identified portion based on a moving average of the blood pressure values of the signal.

In some examples, the processing circuitry is configured to determine the set of mean arterial pressure values by convolving a kernel with the blood pressure values of the signal. The processing circuitry may be configured to determine peaks and/or troughs of the signal based on convolving the kernel and the blood pressure values. The processing circuitry may be configured to convolve two or more kernels with the blood pressure values of the signal to produce two or more convolved signals. The processing circuitry can select the convolved signal with the higher power level and use the kernel associated with the selected signal to determine peaks and/or troughs.

The processing circuitry is configured to use the mean arterial pressure values to determine an autoregulation status of the patient. By using the techniques of this disclosure, the processing circuitry may determine a more accurate, more robust, and more stable set of mean arterial pressure values. The determined set of mean arterial pressure values may be a more accurate representation of the patient state, as compared to a set of mean arterial pressure values determined without the techniques of this disclosure. The techniques of this disclosure may create a more robust set of mean arterial pressure values during events such as motion noise, blood pressure artifacts such as line flushing, and bypass procedures.

The devices, systems, and techniques of this disclosure may allow for presenting a more accurate indication of the autoregulation status of the patient. The presentation of more accurate and more stable information may result in increased confidence by a clinician viewing the presented information, which may lead to more informed decision making by the clinician. A clinician may lose confidence in the information presented by the processing circuitry if the information is less stable and/or less accurate. By determining a set of mean arterial pressure values using the techniques of this disclosure, the processing circuitry may base the determination of autoregulation status on more stable and accurate mean arterial pressure values. By determining an autoregulation status using the techniques of this disclosure, the processing circuitry may reduce swings in the estimates of limits of autoregulation caused by erroneous portions of a blood pressure signal and/or issues caused by cardiopulmonary bypass procedures.

The autoregulation status of a patient may be an indication that the cerebral autoregulation control mechanism of the patient is intact (e.g., functioning properly) or impaired (e.g., not functioning properly). A cerebral autoregulation control mechanism of the body may regulate cerebral blood flow (CBF) over a range of systemic blood pressures. This range of systemic blood pressures may lie within a lower limit of autoregulation (LLA) and an upper limit of autoregulation (ULA). Outside of the LLA and the ULA, blood pressure directly drives CBF, and cerebral autoregulation function may thus be considered impaired.

One method to determine the limits of autoregulation (e.g., the LLA and ULA) noninvasively using near-infrared spectroscopy (NIRS) technology may include the COx measure, which is a moving correlation index between mean arterial pressure (MAP) and regional oxygen saturation ($rSO_2$). The COx measure (e.g., using the Pearson correlation coefficient) is derived from the correlation between $rSO_2$ and MAP. COx relates to the regression line fit or linear correlation between $rSO_2$ and MAP over a time window having a particular length, such as three hundred seconds, in some examples. The COx method may be used to produce a representation of a patient's blood-pressure-dependent autoregulation status.

When the cerebral autoregulation is intact for a patient, there is typically no, or little, correlation between MAP and $rSO_2$. In contrast, MAP and $rSO_2$ typically directly correlate (e.g., the COx value is approximately positive one) when the cerebral autoregulation is impaired. In practice, however, sensed data indicative of autoregulation may be noisy and/or there might be a slightly correlated relationship between variables (e.g., MAP and $rSO_2$) even when cerebral autoregulation is intact for the patient.

Some existing systems for monitoring autoregulation may determine a patient's autoregulation status based on various physiological parameter values (also referred to herein as physiological values), such as arterial blood pressure and oxygen saturation. Measurement of such physiological values may be subject to various sources of error, such as noise caused by relative sensor and patient motion, operator error, poor quality measurements, drugs, or other anomalies. However, some existing systems for monitoring autoregulation may not reduce the various sources of error when utilizing the measured physiological values to determine the patient's autoregulation status. Furthermore, some existing systems may not determine and/or utilize a reliable metric to determine whether the autoregulation status calculated from the physiological values is reliable. Accordingly, the autoregulation status determined by such existing systems may be less accurate or less reliable.

In an intact region of cerebral autoregulation, there may be no correlation between these variables whereas in an impaired region of cerebral autoregulation, the correlation index should approximate unity. In practice, however, the data may be noisy and/or the intact region may exhibit a slightly positive relationship. This positive relationship may render traditional autoregulation limit calculations difficult to perform, resulting in the need for manual interpretation of the data using arbitrary thresholds. Further, the underlying mathematics of the technique may be asymmetric in terms of the results produced for impaired and intact regions and may be, in fact, not computable for the ideal case within the intact region.

A physician may monitor a patient's autoregulation through the use of various monitoring devices and systems that measure various physiological parameters. In certain aspects of the present disclosure, a patient's autoregulation may be monitored by correlating measurements of the patient's blood pressure (e.g., arterial blood pressure) with measurements of the patient's oxygen saturation (e.g., regional oxygen saturation). In particular, a COx value may be derived based at least in part on a linear correlation between the patient's blood pressure and oxygen saturation. In addition, in certain aspects of the present disclosure, the patient's autoregulation may be monitored by correlating measurements of the patient's blood pressure with measurements of the patient's blood volume (e.g., blood volume proxy). In particular, a hemoglobin volume index (HVx) may be derived based at least in part on a linear correlation between the patient's blood pressure and blood volume.

While features of the present disclosure are discussed with reference to COx, in other examples, various other linear correlations such as HVx may be determined to help evaluate a patient's autoregulation status. For example, a linear correlation between measurements of a patient's blood pressure and measurements of a patient's cerebral blood flow may derive a mean velocity index (Mx). As a further example, a linear correlation between measurements of a patient's blood pressure and measurements of a patient's intracranial pressure may derive a pressure reactivity index (PRx). In certain situations, these indices may be utilized to determine or help evaluate a patient's autoregulation. The devices, systems, and techniques of this disclosure can also be applied to the determination of indices such as HVx, Mx, PRx, and/or any other indices, coefficients, and correlations. For example, processing circuitry may be configured to determine an estimate of a limit of autoregulation based on a set of HVx indices, a set of Mx indices, and/or a set of PRx indices.

Additional example details of the parameters that can be used for determining a limit of autoregulation may be found in commonly assigned U.S. Patent Application Publication No. 2016/0367197 filed on Jun. 16, 2016, entitled "Systems and Methods for Reducing Signal Noise When Monitoring Autoregulation," and commonly assigned U.S. Patent Application Publication No. 2017/0105631 filed on Oct. 18, 2016, entitled "System and Method for Providing Blood Pressure Safe Zone Indication During Autoregulation Monitoring," which are incorporated herein by reference in their entirety. A gradients-based method can also be used to determine an estimate of a limit of autoregulation. Processing circuitry can perform a gradients-based method by analyzing a relationship between a change in the patient's blood pressure and a change in the patient's oxygen saturation over a period of time. Additional example details of gradients-based methods are described in commonly assigned U.S. Patent Application Publication No. 2018/0014791 filed Jul. 13, 2017, and entitled "Systems and Methods of Monitoring Autoregulation," the entire content of which is incorporated herein by reference.

FIG. 1 is a conceptual block diagram illustrating an example device 100.

Device 100 includes processing circuitry 110, memory 120, user interface 130, display 132, sensing circuitry 140-142, and sensing device(s) 150-152. In some examples, device 100 may be configured to determine and display the cerebral autoregulation status of a patient, e.g., during a medical procedure or for more long-term monitoring, such as fetal monitoring. A clinician may receive information regarding the cerebral autoregulation status of a patient via display 132 and adjust treatment or therapy to the patient based on the cerebral autoregulation status information.

Device 100 can directly sense the blood pressure of a patient. Additionally, or alternatively, device 100 may receive blood pressure data from a blood pressure device that senses the blood pressure of the patient. Device 100 may directly connect to the blood pressure device and/or a regional oximetry device via wired or wireless communication or indirectly receive data via one or more networks. In this manner, device 100 may be similar to a multi-parametric monitor that receives data from multiple devices. For example, device 100 can directly or indirectly receive data and/or signals from sensing device 150, 151, and/or 152, which may be a part of device 100 or may be separate devices. Device 100 can incorporate all, some, or none of sensing circuitry 140-142 and sensing devices 150-152. Some or all of sensing circuitry 140-142 and sensing devices 150-152 may be located outside of device 100 in separate devices. Device 100 can incorporate all of the data and signals received from sensing devices 150-152 to display autoregulation information.

Processing circuitry 110, as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Memory 120 may be configured to store measurements of physiological parameters, MAP values, $rSO_2$ values, COx values, and value(s) of an LLA and/or a ULA, for example. Memory 120 may also be configured to store data such as blood pressure values, mean arterial pressure values, thresholds, blood pressure variation values, threshold rates, non-bypass conditions, and kernels. The blood pressure values, mean arterial pressure values, thresholds, blood pressure variation values, threshold rates, non-bypass conditions, and/or kernels may stay constant throughout the use of device 100 and across multiple patients, or these values may change over time.

In some examples, memory 120 may store program instructions, which may include one or more program modules, which are executable by processing circuitry 110. When executed by processing circuitry 110, such program instructions may cause processing circuitry 110 to provide the functionality ascribed to it herein. The program instructions may be embodied in software, firmware, and/or RAM-ware. Memory 120 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a patient. For example, processing circuitry 110 may be configured to present blood pressure values, physiological parameter values, and indications of autoregulation status (e.g., cerebral autoregulation status) of a patient via display 132. In some examples, if processing circuitry 110 determines that the autoregulation status of the patient is impaired, then processing circuitry 110 may present a notification (e.g., an alert) indicating the impaired cerebral autoregulation status via display 132. As another example, processing circuitry 110 may present, via display 132, estimates of $rSO_2$ for a patient, an estimate of the blood oxygen saturation ($SpO_2$) determined by processing circuitry 110, pulse rate information, respiration rate information, blood pressure, any other patient parameters, or any combination thereof. Processing circuitry 110 may also be configured to present, via display 132, an indication of whether a signal indicates that the patient is, or was previously, undergoing a cardiopulmonary bypass procedure.

User interface 130 and/or display 132 may include a monitor, cathode ray tube display, a flat panel display such as a liquid crystal (LCD) display, a plasma display, a light emitting diode (LED) display, and/or any other suitable display. User interface 130 and/or display 132 may be part of a personal digital assistant, mobile phone, tablet computer, laptop computer, any other suitable computing device, or any combination thereof, with a built-in display or a separate display. User interface 130 may also include means for projecting audio to a user, such as speaker(s). Processing circuitry 110 may be configured to present, via user interface 130, a visual, audible, tactile, or somatosensory notification (e.g., an alarm signal) indicative of the patient's autoregulation status and/or a notification indicative of the patient's limit(s) of autoregulation.

User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection (e.g., communication interface 290 shown in FIG. 2).

Sensing circuitry 140-142 may be configured to receive physiological signals sensed by respective sensing device(s) 150-152 and communicate the physiological signals to processing circuitry 110. Sensing devices 150-152 and sensing circuitry 140-142 can deliver the physiological signals directly to processing circuitry 110 or sensing circuitry 140-142 can modify the physiological signals (e.g., through pre-processing) before delivering signals to processing circuitry 110. Sensing device(s) 150-152 may include any sensing hardware configured to sense a physiological parameter of a patient, such as, but not limited to, one or more electrodes, optical receivers, blood pressure cuffs, or the like. Sensing circuitry 140-142 may convert the physiological signals to usable signals for processing circuitry 110, such that processing circuitry 110 is configured to receive signals generated by sensing circuitry 140-142. Sensing circuitry 140-142 may receive signals indicating physiological parameters from a patient, such as, but not limited to, blood pressure, regional oxygen saturation, blood volume, heart rate, and respiration. Sensing circuitry 140-142 may include, but are not limited to, blood pressure sensing circuitry, oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140-142 and/or processing circuitry 110 may include signal processing circuitry such as an analog-to-digital converter.

In some examples, oxygen saturation sensing device 150 is a regional oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's forehead and may be used to determine the oxygen saturation of the patient's blood within the venous, arterial, and/or capillary systems of a region underlying the patient's forehead (e.g., in the cerebral cortex).

In such cases, oxygen saturation sensing device 150 may include emitter 160 and detector 162. Emitter 160 may include at least two light emitting diodes (LEDs), each configured to emit at different wavelengths of light, e.g., red or near infrared light. In some examples, light drive circuitry (e.g., within sensing device 150, sensing circuitry 140, and/or processing circuitry 110) may provide a light drive signal to drive emitter 160 and to cause emitter 160 to emit light. In some examples, the LEDs of emitter 160 emit light in the wavelength range of about 600 nanometers (nm) to about 1,000 nm. In a particular example, one LED of emitter 160 is configured to emit light at a wavelength of about 730 nm and the other LED of emitter 160 is configured to emit light at a wavelength of about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160. Light intensity of multiple wavelengths may be received at both the "close" and the "far" detector 162. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time. Oxygen saturation sensing device 150 may provide the regional oxygen saturation signal to processing circuitry 110 or to any other suitable processing device to enable evaluation of the patient's autoregulation status.

In operation, blood pressure sensing device 151 and oxygen saturation sensing device 150 may each be placed on the same or different parts of the patient's body. For example, blood pressure sensing device 151 and oxygen saturation sensing device 150 may be physically separate from each other and may be separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional oxygen saturation. One or both of blood pressure sensing device 151 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). For example, blood pressure sensing device 151 may include a blood pressure cuff for non-invasively monitoring blood pressure or an arterial line for invasively monitoring blood pressure. In certain examples, blood pressure sensing device 151 may include one or more pulse oximetry sensors. In some such cases, the patient's blood pressure may be derived by processing time delays between two or more characteristic points within a single plethysmography (PPG) signal obtained from a single pulse oximetry sensor. In some examples, sensing devices 150, 151, and/or 152 deliver data to a multi-parametric monitor that can sense blood pressure and/or oxygen saturation of a patient. A tablet or other computing device can also be configured to receive data and/or signals from sensing devices 150, 151, and/or 152, where the data and/or signals indicate blood pressure and/or oxygen saturation of the patient.

Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, and entitled "Systems and Methods for Non-Invasive Blood Pressure Monitoring," the entire content of which is incorporated herein by reference. In other cases, the patient's blood pressure may be continuously, non-invasively monitored via multiple pulse oximetry sensors placed at multiple locations on the patient's body. As described in commonly assigned U.S. Pat. No. 6,599,251, entitled "Continuous Non-invasive Blood Pressure Monitoring Method and Apparatus," the entire content of which is incorporated herein by reference, multiple PPG signals may be obtained from the multiple pulse oximetry sensors, and the PPG signals may be compared against one another to estimate the patient's blood pressure. Regardless of its form, blood pressure sensing device 151 may be configured to generate a blood pressure signal indicative of the patient's blood pressure (e.g., arterial blood pressure) over time. Blood pressure sensing device 151 may provide the blood pressure signal to sensing circuitry 141, processing circuitry 110, or to any other suitable processing device to enable evaluation of the patient's autoregulation status.

Sensing circuitry 141 may be configured to generate a signal indicative of a blood pressure of a patient based on a physiological signal sensed by sensing device 151. Processing circuitry 110 may be configured to timestamp the received signal to account for possible missing periods of signal and to allow the possibility to synchronize the processed signal with other parameters (e.g., signals received from sensing circuitry 140 or 142). In some examples, the sampling frequency for the signal received from sensing circuitry 141 is one hundred hertz, although other sampling frequencies are possible. Based on the received signal, processing circuitry 110 may be configured to determine mean arterial pressure values at an output rate of one hertz, although other output rates for mean arterial pressure values are possible. The signal received by processing circuitry 110 from sensing circuitry 141 may be referred as a raw signal, an unfiltered signal, and/or a blood pressure signal. In other examples, processing circuitry 110 may directly receive a signal (e.g., analog or digital signal) from an external (such as blood pressure sensing device 151) that is indicative of the blood pressure without further processing and/or sensing circuitry 141. In other examples, processing circuitry 110 may perform some or all of the processes attributable to sensing circuitry 141 described herein.

Processing circuitry 110 may be configured to determine mean arterial pressure values based on a sampling window of, e.g., five or ten seconds for the blood pressure values in the signal received from sensing circuitry 141. Processing circuitry 110 may also be configured to determine systolic pressure, diastolic pressure, and heart rate signals using the sampling window. Processing circuitry 110 may be configured to associate one or more flags with each portion of the signal to identify the portion as bypass, to identify the event of a possible artifact, to identify a pulsatile signal, or identify a disconnection of sensing device 151 from the patient. For example, processing circuitry 110 may be configured to identify a portion of the signal including a characteristic that exceeds a threshold and to set a flag for the identified portion. Processing circuitry 110 may be configured to determine beat-to-beat signal information, containing a time stamp associated with each beat, systolic pressure, diastolic pressure, and beat duration. Processing circuitry 110 can integrate the arterial blood pressure over the cardiac cycle to provide a more accurate measure. Alternatively, processing circuitry 110 can calculate a mean arterial pressure value as the average value over a fixed moving window, which can be useful in anomalous conditions (e.g., arrhythmia, unusual beat shapes, and/or heart problems), when beat-to-beat pulse identification is problematic or not possible.

Figure 11:
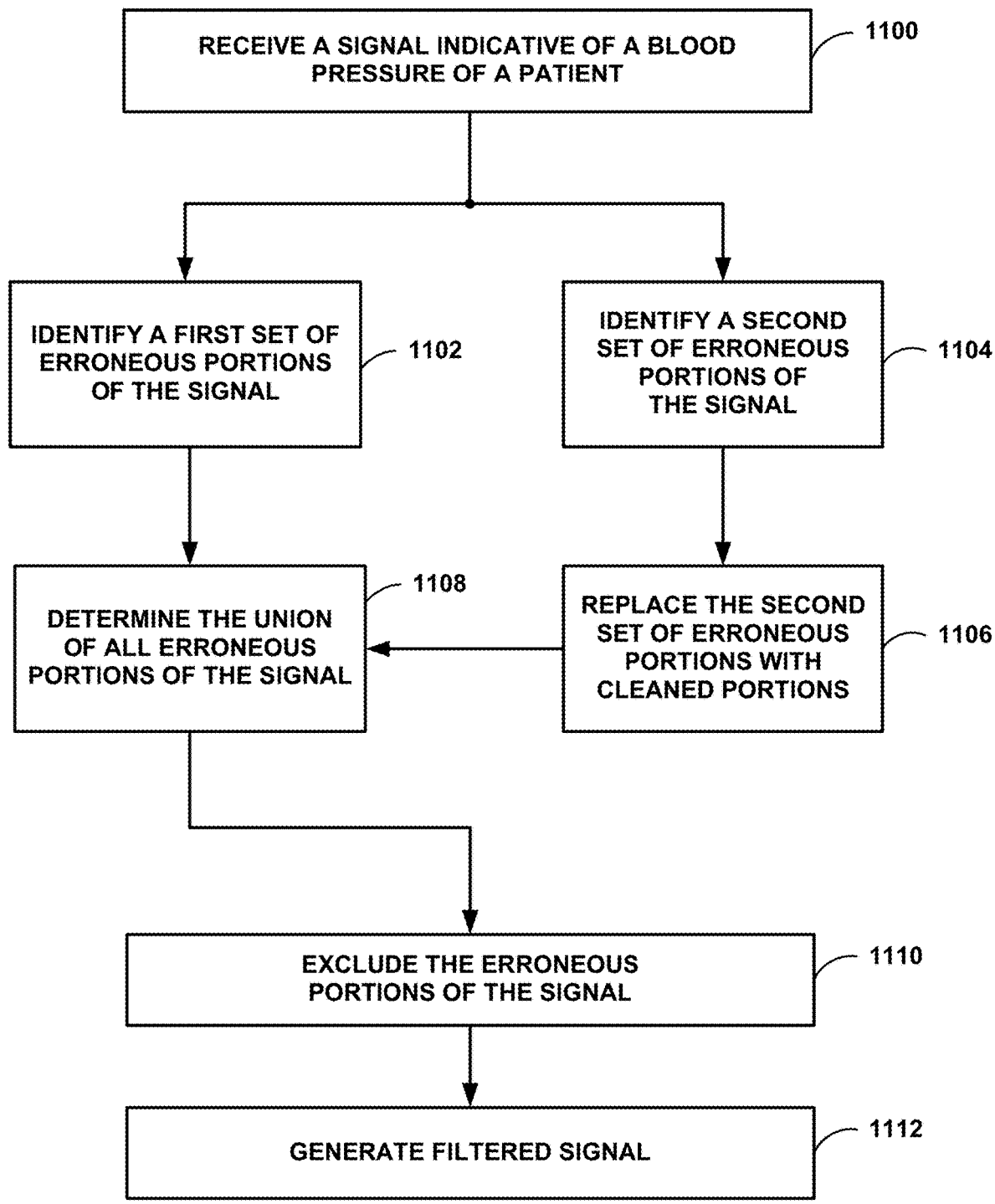

From a high-level perspective, processing circuitry 110 can determine mean arterial pressure values using three steps, as shown in FIG. 11. First, processing circuitry 110 can clean or filter the arterial blood pressure signal received from sensing circuitry 141 by identifying artifacts in the raw signal. Depending on the artifacts and characteristics of a portion of the signal, processing circuitry 110 may be configured to exclude or modify the portion of the signal during the cleaning or filtering process. By excluding or modifying one or more portions of the signal, processing circuitry 110 can generate a filtered signal.

Second, processing circuitry 110 may be configured to identify a portion of the filtered signal as pulsatile or as indicating that the patient is undergoing a cardiopulmonary bypass procedure. Processing circuitry 110 can identify a portion of the filtered signal as pulsatile or bypass based on characteristics such as the power of the filtered signal, a diastolic value, a prediction value, and one or more non-bypass conditions. Processing circuitry 110 can use a portion of a filtered signal or a portion of an unfiltered signal to determine whether the portion is pulsatile or indicates that the patient is undergoing a cardiopulmonary bypass procedure.

Third, processing circuitry 110 may be configured to determine a set of mean arterial pressure values based on the filtered signal. In examples in which processing circuitry 110 identifies a portion of the signal as pulsatile, processing circuitry 110 may be configured to determine mean arterial pressure values using beat-to-beat information. Processing circuitry 110 can determine beat-to-beat information at least in part by convolving a kernel and the blood pressure values of the signal and determining signal peaks or troughs based on the convolved signal. In examples in which processing circuitry 110 identifies a portion of the signal as indicating a bypass procedure, processing circuitry 110 may be configured to determine mean arterial pressure values using a moving average of the blood pressure signal.

Processing circuitry 110 may be configured to determine a set of correlation coefficient values based on the set of mean arterial pressure values and a set of oxygen saturation values. Processing circuitry 110 can determine an estimate of a limit of autoregulation of a patient based on the set of correlation coefficient values. The correlation coefficient values may be near positive one at very low values and very high blood pressure values. Therefore, to determine an estimate of the lower limit of autoregulation, processing circuitry 110 may determine the lowest blood pressure value at which the associated correlation coefficient values are below a threshold level, such as 0.8, 0.7, 0.6, 0.5, 0.4, 0.3, 0.2, 0.1, or 0.0, where full correlation is approximately 1.0 and no correlation is approximately 0.0. To determine an estimate of the upper limit of autoregulation, processing circuitry 110 may determine the highest blood pressure value at which the associated correlation coefficient values are below a threshold level.

Processing circuitry 110 is also configured to determine an autoregulation status of the patient based on the mean arterial pressure values. For example, processing circuitry 110 may determine whether the current mean arterial pressure value of the patient is greater than the estimate of the lower limit of autoregulation. If the current mean arterial pressure value is greater than the estimate of the lower limit of autoregulation, then processing circuitry 110 can determine that the patient has intact autoregulation, unless the current mean arterial pressure value is greater than the upper limit of autoregulation of the patient.

Processing circuitry 110 may be configured to output, for display via display 132 of user interface 130, an indication of the autoregulation status. To present an indication of autoregulation status, display 132 may present a graphical user interface such as graphical user interface 300 shown in FIG. 3. As described in further detail below, graphical user interface 300 includes an indicator of autoregulation status 350. The indication of autoregulation status may include text, colors, and/or audio presented to a user. Processing circuitry 110 may be further configured to present an indication of one or more limits of autoregulation (e.g., indicators 360 and 370).

By determining a set of mean arterial pressure values using the techniques of this disclosure, processing circuitry 110 can determine more accurate and more stable mean arterial pressure values, as well as more accurate determinations of correlation and co-trending with other parameters. By using more accurate mean arterial pressure values, processing circuitry 110 can make more accurate determinations of the autoregulation status of the patient.

The techniques of this disclosure are described with respect to processing circuitry 110 of device 100. However, in some examples, some or all of the functionality attributed to processing circuitry 110 may be performed by processing circuitry in a separate blood pressure sensing device that includes sensing circuitry 141 and/or sensing device 151. The blood pressure sensing device may be an external device that delivers data and/or signals to a multi-parametric monitor. The external device can be coupled to processing circuitry 110 of device 100.

Although other example devices, systems, and techniques are possible, device 100 may be configured to determine an autoregulation status of a patient based on correlation coefficient values derived from mean arterial pressure values and oxygen saturation values. Alternatively, processing circuitry 110 may determine the first estimate of the limit of autoregulation based on HVx values, BVS values, and/or oxygen saturation values. Regional oximetry device 200 of FIG. 2 includes additional detail on how processing circuitry 110 can determine oxygen saturation values based on a physiological signal received from sensing device 150.

Figure 2:
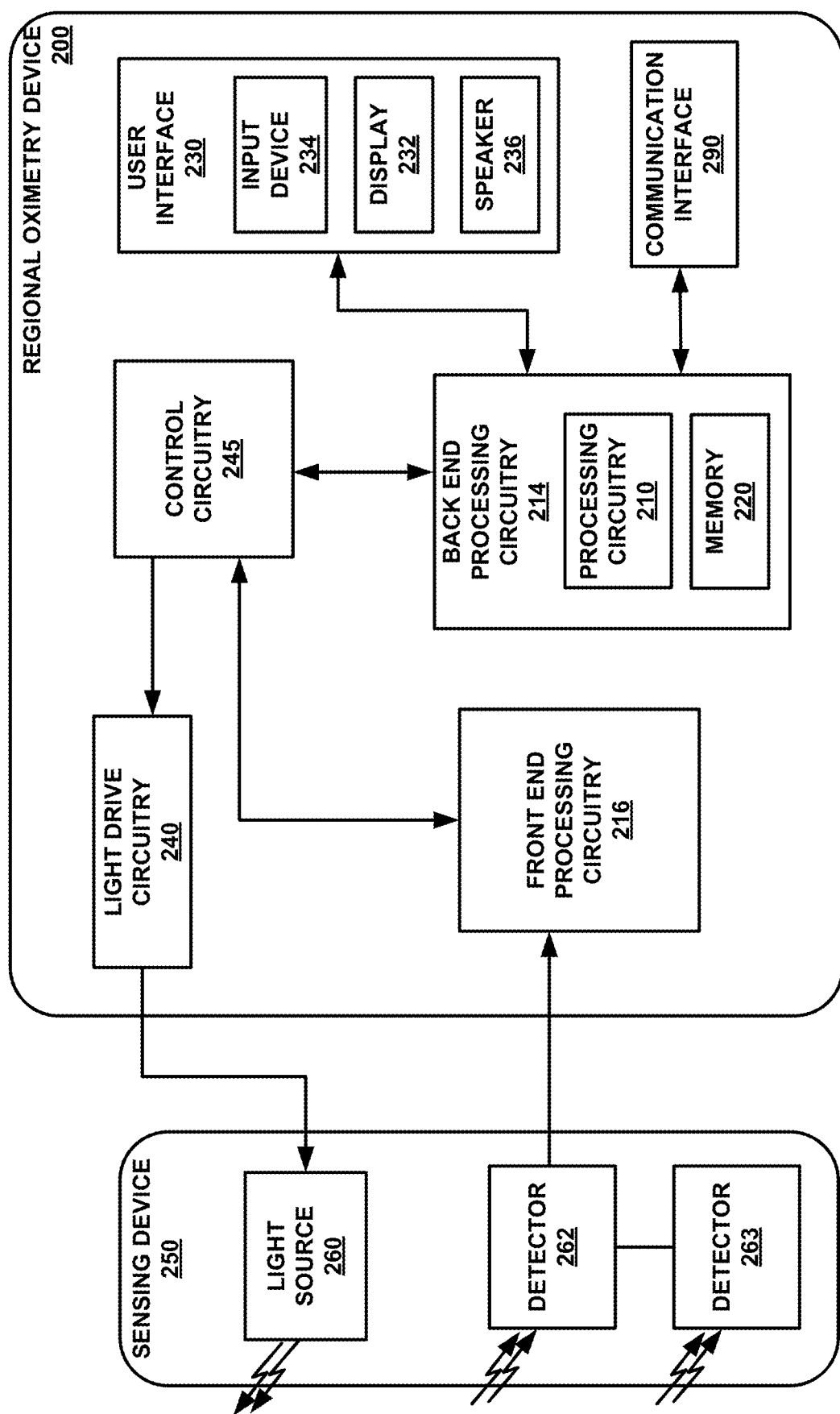
FIG. 2 is a conceptual block diagram illustrating an example regional oximetry device for monitoring the autoregulation status of a patient.

FIG. 2 is a conceptual block diagram illustrating an example regional oximetry device 200 for monitoring the autoregulation status of a patient. In the example shown in FIG. 2, regional oximetry device 200 is coupled to sensing device 250 and may be collectively referred to as a regional oximetry system, which each generate and process physiological signals of a subject. In some examples, sensing device 250 and regional oximetry device 200 may be part of an oximeter. As shown in FIG. 2, regional oximetry device 200 includes back-end processing circuitry 214, user interface 230, light drive circuitry 240, front-end processing circuitry 216, control circuitry 245, and communication interface 290. Regional oximetry device 200 may be communicatively coupled to sensing device 250. Regional oximetry device 200 is an example of device 100 shown in FIG. 1.

In some examples, regional oximetry device 200 may also include a blood pressure sensor and/or a blood volume sensor (e.g., sensing devices 151 and 152 shown in FIG. 1). The blood pressure sensor may be an external blood pressure device that can deliver data and/or signals to a regional oximetry device or a multi-parametric monitor. The blood pressure sensor can also be a part of device 200, as shown in FIG. 1 with respect to device 100. In some examples, sensing device 250 may be a separate device that is external to regional oximetry device 200, rather than a device that is part of regional oximetry device 200.

In the example shown in FIG. 2, sensing device 250 includes light source 260, detector 262, and detector 263. In some examples, sensing device 250 may include more than two detectors. Light source 260 may be configured to emit photonic signals having two or more wavelengths of light (e.g., red and infrared (IR)) into a subject's tissue. For example, light source 260 may include a red light emitting light source and an IR light emitting light source, (e.g., red and IR light emitting diodes (LEDs)), for emitting light into the tissue of a subject to generate physiological signals. In some examples, the red wavelength may be between about 600 nm and about 700 nm, and the IR wavelength may be between about 800 nm and about 1,000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1,000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

In some examples, detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 262 and 263.

After converting the received light to an electrical signal, detectors 262 and 263 may send the detection signals to regional oximetry device 200, where the detection signals may be processed and physiological parameters may be determined (e.g., based on the absorption of the red and IR wavelengths in the subject's tissue at both detectors). In some examples, one or more of the detection signals may be preprocessed by sensing device 250 before being transmitted to regional oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110. Processing circuitry 210 may receive and further process one or more signals received from front-end processing circuitry 216. For example, processing circuitry 210 may determine physiological parameter values based on the received signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or regional oximetry device 200.

Processing circuitry 210 is an example of processing circuitry 110 and is configured to perform the techniques of this disclosure. For example, processing circuitry 210 is configured to receive signals indicative of physiological parameters including a blood pressure of the patient. For example, processing circuitry 210 can identify a first portion of a signal indicating blood pressure of the patient, where the first portion includes a first characteristic that exceeds a first threshold. Processing circuitry 210 may also identify a second portion of the signal including a second characteristic that exceeds a second threshold. Processing circuitry 210 may then determine a filtered signal by excluding or modifying the first portion and the second portion. Processing circuitry 210 may determine a set of mean arterial pressure values based on the filtered signal.

Processing circuitry 210 can determine the autoregulation status of the patient based on the set of mean arterial pressure values. For example, processing circuitry 210 is also configured to determine values of physiological parameters based on the signals and determine correlation coefficient values based on the values of the physiological parameters. Processing circuitry 210 can determine correlation coefficients based on values of mean arterial pressure and values of oxygen saturation. Processing circuitry 210 may determine a limit of autoregulation based on a set of correlation coefficient values. To determine the autoregulation status of the patient, processing circuitry 210 can compare the current mean arterial pressure value to the limit of autoregulation.

Memory 220 may include any suitable computer-readable media capable of storing information that can be interpreted by processing circuitry 210. In some examples, memory 220 may store measurements of physiological parameters, mean arterial pressure values, oxygen saturation values, correlation coefficient values, threshold rates, threshold values, threshold time durations, blood pressure variation values, predetermined ranges of variation, maximum and minimum blood pressure values, threshold rates, non-bypass conditions, and kernels, any other determined values, or any combination thereof, in a memory device for later retrieval. Back-end processing circuitry 214 may be communicatively coupled with user interface 230 and communication interface 290.

User interface 230 may include input device 234, display 232, and speaker 236. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include any type of user input device such as a keyboard, a mouse, a touch screen, buttons, switches, a microphone, a joy-stick, a touch pad, or any other suitable input device or combination of input devices. In other examples, input device 234 may be a pressure-sensitive or presence-sensitive display that is included as part of display 232. Input device 234 may also receive inputs to select a model number of sensing device 250, blood pressure sensor 250 (FIG. 2), or blood pressure processing equipment. In some examples, processing circuitry 210 may determine a threshold rate and/or a length of a window of time based on user input received from input device 234.

Figure 3:
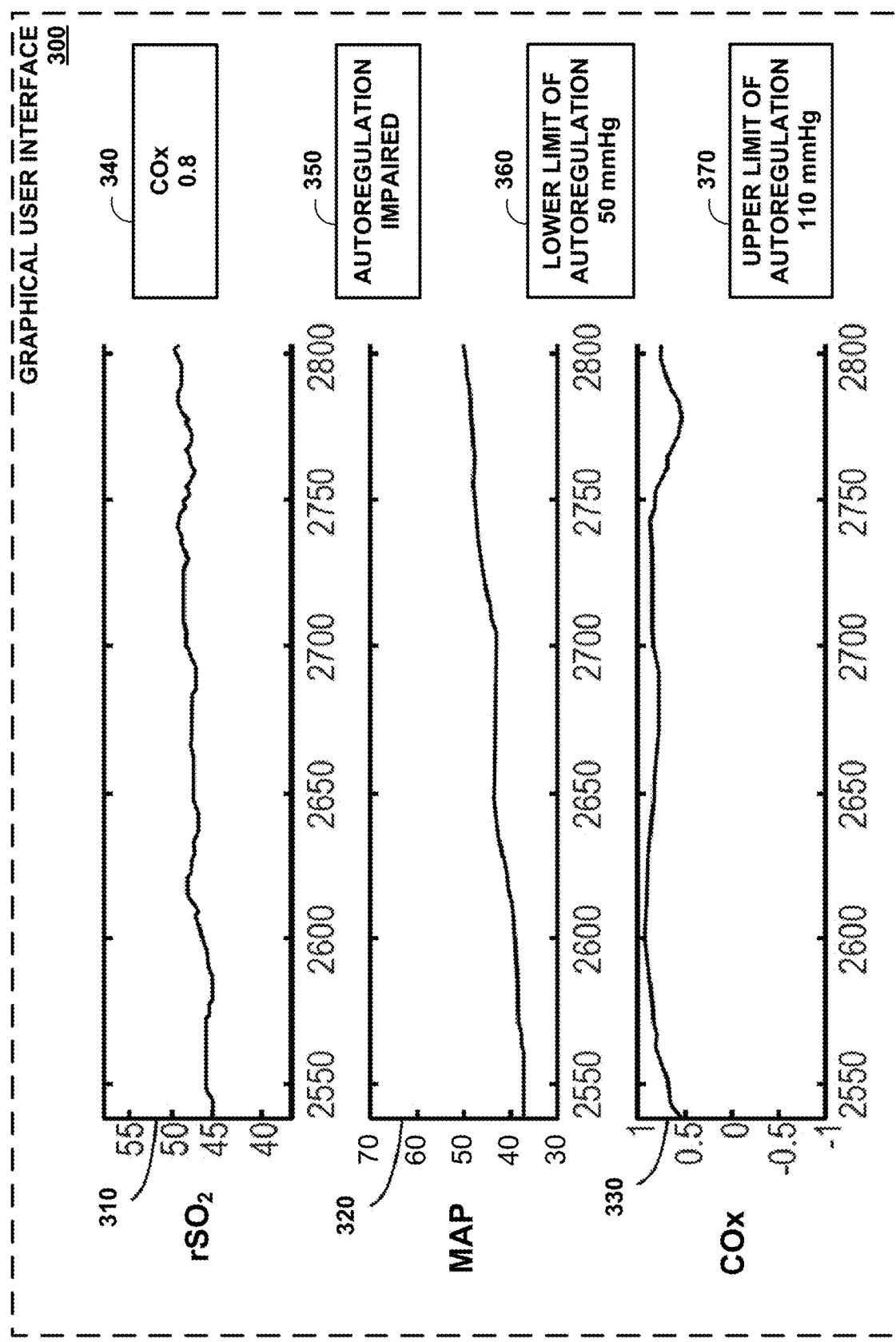
FIG. 3 illustrates an example graphical user interface including autoregulation information presented on a display.

In some examples, the subject may be a medical patient and display 232 may exhibit a list of values which may generally apply to the subject, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2. Additionally, display 232 may present, for example, one or more estimates of a subject's regional oxygen saturation generated by regional oximetry device 200 (referred to as an "rSO₂" measurement). Display 232 may also present indications of the upper and lower limits of autoregulation. Speaker 236 within user interface 230 may provide an audible sound that may be used in various examples, such as for example, sounding an audible alarm in the event that the autoregulation status of a patient is impaired or that the patient's physiological parameters are not within a predefined normal range.

Communication interface 290 may enable regional oximetry device 200 to exchange information with external devices. Communication interface 290 may include any suitable hardware, software, or both, which may allow regional oximetry device 200 to communicate with electronic circuitry, a device, a network, a server or other workstations, a display, or any combination thereof. For example, regional oximetry device 200 may receive MAP values and/or oxygen saturation values from an external device via communication interface 290.

The components of regional oximetry device 200 that are shown and described as separate components are shown and described as such for illustrative purposes only. In some examples the functionality of some of the components may be combined in a single component. For example, the functionality of front-end processing circuitry 216 and back-end processing circuitry 214 may be combined in a single processor system. Additionally, in some examples the functionality of some of the components of regional oximetry device 200 shown and described herein may be divided over multiple components. For example, some or all of the functionality of control circuitry 245 may be performed in front-end processing circuitry 216, in back-end processing circuitry 214, or both. In other examples, the functionality of one or more of the components may be performed in a different order or may not be required. In some examples, all of the components of regional oximetry device 200 can be realized in processor circuitry.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Graphical user interface 300 may be configured to display various information related to blood pressure, oxygen saturation, the COx index, limits of autoregulation, and/or autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of device 100. Processing circuitry 110 can use the set of MAP values determined from a filtered signal for presenting as blood pressure signal indicator 320. However, processing circuitry 110 may be configured to use a different set of data for presenting as blood pressure signal 320. In some examples, processing circuitry 110 uses the set of MAP values determined from the filtered signal only for determining correlation coefficient values.

For example, processing circuitry 110 can identify portions of the blood pressure signal with characteristics that exceed a threshold. Processing circuitry 110 can exclude or modify the identified portions to create a filtered signal. Processing circuitry 110 may then use the filtered signal to determine a set of MAP values. Processing circuitry 110 can identify a portion of the blood pressure signal indicating that the patient is undergoing a cardiopulmonary bypass procedure and use a moving average to determine MAP values. In some examples, to determine the set of MAP values, processing circuitry 110 determines signal peaks based on convolving the filtered signal with a kernel.

In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present rSO₂ values and COx values, respectively, as discrete points, in a table, as a moving average, as a waveform, and/or as a single value.

COx signal indicator 330 may present a set of correlation coefficient values determined by processing circuitry 110. Processing circuitry 110 may determine the correlation coefficient values as a function of the oxygen saturation values presented in oxygen saturation signal indicator 310 and the MAP values presented in blood pressure signal indicator 320. In some examples, a COx value at or near one indicates the autoregulation status of a patient is impaired, as shown in autoregulation status indicator 350.

Processing circuitry 110 may determine a set of correlation coefficient values and associated blood pressure values using the values presented in indicators 310, 320, and/or 330. Processing circuitry 110 may be configured to determine an estimate of a limit of autoregulation based on correlation coefficient values across a time window for data collection. For example, the length of the time window may be one, two, or three hundred seconds.

COx value indicator 340 shows a COx value of 0.8, which may result in a determination by processing circuitry 110 that the autoregulation status of the patient is impaired. Processing circuitry 110 may be configured to present, as the COx value in COx value indicator 340, the most recently determined COx value or a moving average of recently determined COx values. To determine the autoregulation status of a patient for presentation in autoregulation status indicator 350, processing circuitry 110 may determine whether the most recent MAP value shown in blood pressure signal indicator 320 is between the limits of autoregulation presented in limit of autoregulation indicators 360 and 370.

Processing circuitry 110 may present limit of autoregulation indicators 360 and/or 370 in terms of blood pressure, for example, mmHg. Processing circuitry 110 can determine the limits of cerebral autoregulation (LLA and ULA) for presentation in indicators 360 and 370 based on a relationship between the blood pressure of a patient and another physiological parameter of the patient. For example, indicator 350 and/or indicator 360 may be highlighted when the LLA has been exceeded or indicator 360 may be highlighted when the ULA has been exceeded. In other examples, a single indicator may present the type of limit that has been exceed by the MAP value. If the LLA or ULA change, processing circuitry 110 may control user interface 300 to change the value of the LLA or ULA in accordance with any change to that respective value.

Processing circuitry 110 may determine an estimate of a lower limit of autoregulation presented in indicator 360 and/or an estimate of an upper limit of autoregulation presented in indicator 370. Processing circuitry 110 may determine the estimates based on a set of correlation coefficient values including one or more updated values. Processing circuitry 110 may be configured to generate a notification in response to determining that the MAP value is less than or equal to the estimate of the lower limit of autoregulation. Processing circuitry 110 may output the notification in autoregulation status indicator 350 as text, color, blinking, and/or any other suitable visible or audible manner.

Figure 4:
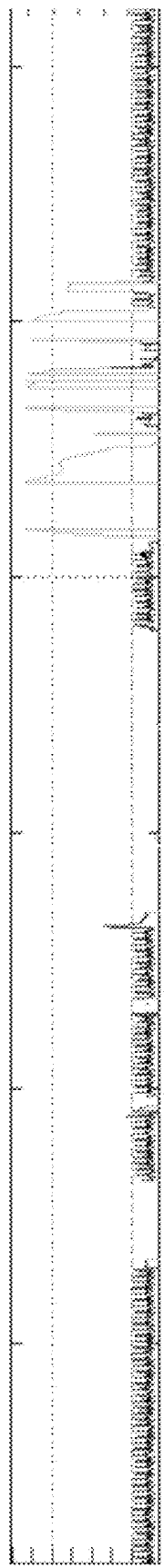

FIGS. 4, 5, 6, 7, and 8 are example graphs showing bypass and pulsatile (e.g., non-bypass) signals. For each of FIGS. 4-8, the x-axis represents time, and the y-axis represents blood pressure, which may be expressed in millimeters of mercury. FIG. 4 shows a graph of arterial blood pressure with periods 420, 430, and 440 of line flushing. During periods 420, 430, and 440, the light gray line representing arterial blood pressure can rise well beyond normal levels. For example, if the normal levels of blood pressure are less than one hundred and fifty millimeters of mercury, during periods 420, 430, and 440 the blood pressure may be greater than two hundred millimeters of mercury or greater than three hundred millimeters of mercury.

The graph of FIG. 4 also shows periods 400 and 410 where the arterial blood pressure has an intermittent signal. The graph shows no signal during periods 400 and 410 because the processing circuitry of a device (e.g., device 100) or another blood pressure device can remove invalid regions and calculate MAP values only for the valid signal. Thus, during periods 400 and 410, the processing circuitry may determine that the signal either has no blood pressure value or that the signal has a blood pressure value that cannot be determined. In examples in which the processing circuitry identifies portions of the signal associated with periods 400, 410, 420, 430, and 440, the processing circuitry can exclude the portions from the determination of a filtered signal. The processing circuitry may be configured to modify some or all of the portions and use the modified blood pressure values to determine a filtered signal.

Figure 5:
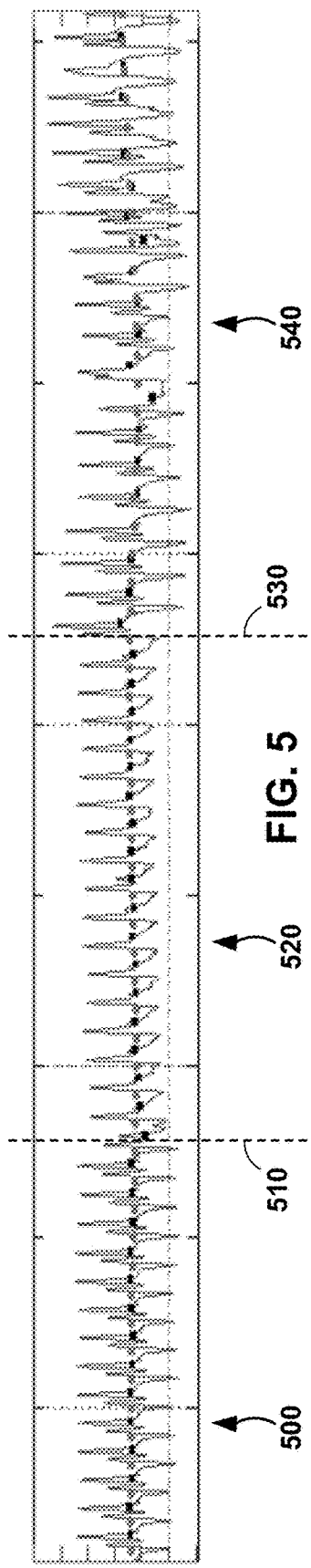

FIG. 5 shows a graph of a blood pressure signal with an abnormal heart beat morphology changing into a regular heart beat morphology. For example, the blood pressure signal has an abnormal heart beat morphology during periods 500 and 540. The blood pressure signal has a normal heart beat morphology during period 520. Time 510 is the dividing point between periods 500 and 520, and time 530 is the dividing point between periods 520 and 540. Processing circuitry that uses a beat-to-beat algorithm for periods 500 and 540 may be less accurate than processing circuitry that uses a moving average function. An example moving average function may have a five-second window or a ten-second window.

Processing circuitry of this disclosure may be configured to use different techniques for determining mean arterial pressure values for portions associated with different beat morphologies. For example, responsive to identifying period 500 as having an abnormal beat morphology, the processing circuitry may be configured to determine mean arterial pressure values using a moving average. Responsive to identifying period 500 as having a normal beat morphology, the processing circuitry may be configured to determine mean arterial pressure values using beat-to-beat information.

Figure 6:
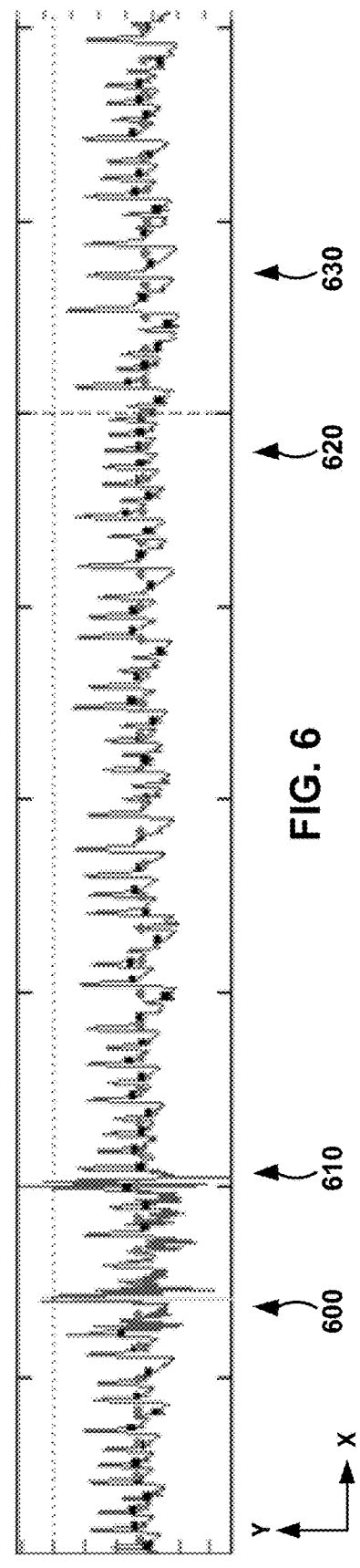

FIG. 6 shows a graph of a blood pressure signal with an irregular heartbeat morphology. During periods 600 and 610, the blood pressure signal has sharp variations in the diastolic/systolic components. The blood pressure signal also has sharp variations in the duration of each heartbeat. For example, during period 620, the blood pressure signal has a relatively high beat frequency. During period 630, the blood pressure signal has a relatively low beat frequency. The blood pressure signal also has a substantial amount of noise in the signal between period 600 and period 610. Processing circuitry that uses a moving-average algorithm for the blood pressure signal shown in FIG. 6 to determine MAP values may more accurately determine the autoregulation status of the patient, as compared to processing circuitry that uses a beat-to-beat algorithm. For example, the abnormal beat morphologies and high noise levels during periods 600 and 610 may result in less accurate mean arterial pressure values when using beat-to-beat techniques. Less accurate mean arterial pressure values can result in less accurate determinations of the autoregulation status of a patient.

FIG. 7 shows a graph of a blood pressure signal during bypass and non-bypass periods. During period 700, the blood pressure signal has a relative high power level, which indicates that the patient is pulsatile (e.g., non-bypass). After time 710, the blood pressure signal has a relative low power level, which indicates that the patient is undergoing a cardiopulmonary bypass procedure. During period 720, the blood pressure signal briefly has a relatively high power level, which indicates that the patient is pulsatile. After time 730, the blood pressure signal has a relative high power level, which indicates that the patient is again pulsatile and no longer undergoing bypass. Processing circuitry may be configured to apply an algorithm to the blood pressure signal shown in FIG. 7 to determine whether the patient is undergoing a cardiopulmonary bypass procedure. Processing circuitry of this disclosure can use a moving average to determine mean arterial pressure values for portions of the signal indicating a cardiopulmonary bypass procedure (e.g., between times 710 and 730), which may be more accurate than using beat-to-beat techniques.

FIG. 8 shows a graph of a blood pressure signal during bypass and non-bypass periods. The graph of FIG. 8 shows a zoomed-in portion of the blood pressure signal shown in FIG. 7. During period 800, the blood pressure signal has a relative high power level, which indicates that the patient is pulsatile. During period 820, the blood pressure signal has a relatively low power level, which indicates that the patient is undergoing a cardiopulmonary bypass procedure. Time 810 is approximately the dividing line between periods 800 and 820. The power level of a signal may be proportional to the amplitude of the signal. Thus, the amplitude of the blood pressure signal is higher during period 800 than the amplitude during period 820.

Processing circuitry of this disclosure may be configured to determine whether a patient is undergoing a cardiopulmonary bypass procedure based on the power level of the blood pressure signal. The processing circuitry can use other techniques for determining that the patient is undergoing a cardiopulmonary bypass procedure, such as the techniques described with respect to FIGS. 12-14. Responsive to the determination of whether the patient is undergoing a cardiopulmonary bypass procedure, the processing circuitry can use different techniques for determining mean arterial pressure values.

FIGS. 9A, 9B, 9C, and 9D are graphs illustrating example kernels. Each of kernels 900, 910, 920, and 930 may be adaptable kernels. The processing circuitry of a regional oximetry device or a blood pressure sensing device can select the parameters of kernels 900, 910, 920, and 930 as a function of the heart rate of the patient. Each of kernels 900, 910, 920, and 930 can be non-symmetrical with variable lengths that the processing circuitry can select according to signal morphology. The x-axis of each graph of FIGS. 9A-9D represents the number of samples of the blood pressure signal, and the y-axis represents the relative weight of each sample.

The processing circuitry may be configured to use the blood pressure signal to create kernels 900, 910, 920, and 930 to enhance or mitigate certain beat features in the blood pressure signal. The processing circuitry can use kernels 900, 910, 920, and 930 to determine trends of the mean arterial pressure of the patient. The determination of trends in the mean arterial pressure may be useful, for example, for cardiac patients with abnormal heart beat morphologies, as shown in FIGS. 5 and 6.

In some examples, the processing circuitry creates and modifies kernels 900, 910, 920, and 930 adaptively from the arterial blood pressure signal. The processing circuitry can use the adaptive kernels 900, 910, 920, and 930 for the detection and/or mitigation of unusual heart beat features in the blood pressure signal. The processing circuitry may select or modify kernels 900, 910, 920, and 930 based on an estimate of the heart rate of the patient and/or based on other blood pressure parameters of the patient.

A kernel may include a number of phases, such as a first plateau, an upslope, a second plateau, a downslope, and a third plateau (e.g., kernels 910, 920, and 930). The processing circuitry can dynamically change the number of phases of a kernel. The processing circuitry can select the number of samples for each kernel phase based on beat morphology, heart rate, harmonic decomposition, and/or any other parameter of the blood pressure signal. The value of the kernel for each phase may be predetermined or may be a function of the features and parameters of the blood pressure signal.

The processing circuitry can dynamically adjust the height or weighting (e.g., the y-axis direction of FIGS. 9A-9D) of each point on one of kernels 900, 910, 920, and 930. In some examples, the processing circuitry dynamically adjust the length (e.g., the x-axis direction of FIGS. 9A-9D) of kernels 900, 910, 920, and 930, such that a kernel can be adapted to the most likely beat duration. A single heart beat can last thirty samples, forty samples, fifty samples, or any other number of samples. In some examples, kernels 900, 910, 920, and 930 can also be non-symmetrical kernels that can emphasize and enhance universal beat characteristics. The processing circuitry can adapt the parameters used to construct each non-symmetrical kernel.

The processing circuitry can use kernels to detect systolic peaks and diastolic troughs in the blood pressure signal. A first kernel may have a higher cross-correlation with a first type of beat morphology, while a second kernel may have a higher cross-correlation with a second type of beat morphology. Thus, the processing circuitry can convolve the blood pressure signal with multiple kernels and use the kernel that best fits or matches the beat morphology. The processing circuitry can select a kernel and use the selected kernel to detect peaks and troughs. The processing circuitry can also use the selected kernel to determine heart beats and to determine the heart rate of the patient. The processing circuitry may then determine mean arterial pressure values based on the peaks, troughs, and heart beats.

The processing circuitry can also generate a quality metric from the determination of mean arterial pressure value. In examples in which more filtering is required for a segment of the blood pressure signal, the processing circuitry may determine a lower quality metric, as compared to a segment that requires less filtering. The processing circuitry can use the quality metric to weight the confidence in the autoregulation algorithm. In examples in which the quality metric is relatively high, then the processing circuitry can assign a higher confidence level to an estimate of the autoregulation status of the patient.

The processing circuitry can create several kernels to enhance detection of systolic or diastolic peak components. Each kernel may enhance beat characteristics close to the point of interest, such as the systolic peak or the diastolic trough. The processing circuitry can use one kernel in the extraction of the diastolic pressure and can use another kernel to extract the systolic pressure. The processing circuitry may use template matching where the template is predefined from a model of the range of possible heartbeat morphologies. The processing circuitry may be configured to decompose the blood pressure signal into a time-frequency representation before using kernels 900, 910, 920, and 930 or template matching.

FIGS. 10, 11, 12, 13, 14, 15, and 16 are flow diagrams illustrating example techniques for determining a set of mean arterial pressure values, in accordance with some examples of this disclosure. Although FIGS. 10-16 are described with respect to processing circuitry 110 of device 100 (FIG. 1), in other examples, processing circuitry 210, 214, and/or 216 (FIG. 2), alone or in combination with processing circuitry 110, may perform any part of the techniques of FIGS. 10-16.

Figure 10:
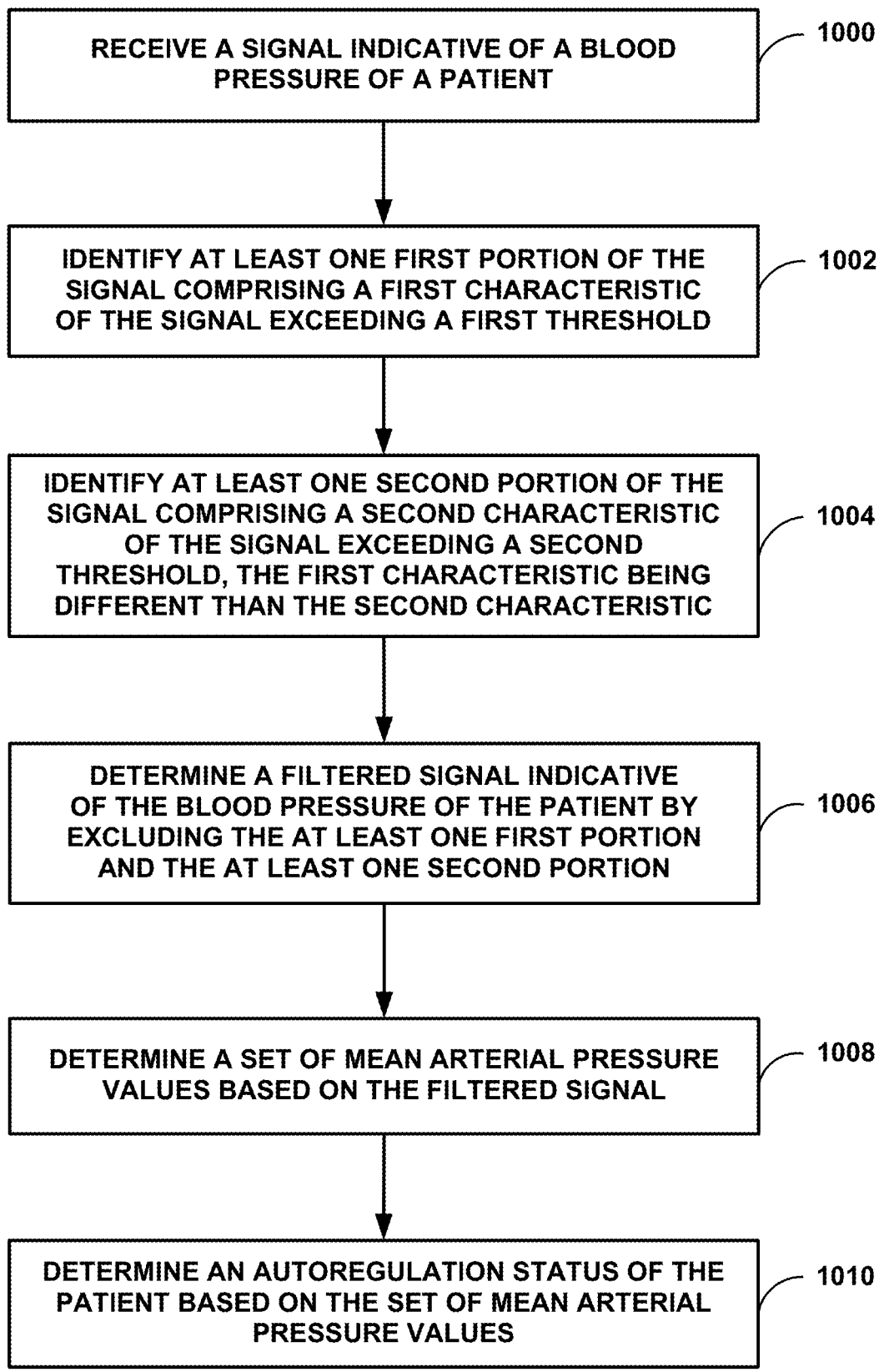
FIGS. 10, 11, 12, 13, 14, 15, and 16 are flow diagrams illustrating example techniques for determining a set of mean arterial pressure values, in accordance with some examples of this disclosure.

In the example of FIG. 10, processing circuitry 110 receives a signal from sensing circuitry 141 indicative of a blood pressure of a patient (1000). The signal may include an arterial blood pressure signal of the patient. Processing circuitry 110 then identifies at least one first portion of the signal comprising a first characteristic of the signal exceeding a first threshold (1002). Processing circuitry 110 also identifies at least one second portion of the signal comprising a second characteristic of the signal exceeding a second threshold, the first characteristic being different than the second characteristic (1004).

Processing circuitry 110 can process the signal to determine clean, valid segments for trend analysis. Processing circuitry 110 can use these clean segments in the subsequent calculation of the mean arterial pressure. Processing circuitry 110 identifies the at least one first portion and the at least one second portion as unclean segments for exclusion from the determination of mean arterial pressure. Processing circuitry 110 can use a combination of signal features and characteristics to identify these portions, such as maximum allowable blood pressure values; minimum allowable blood pressure values; thresholds for the minimum and maximum differences between consecutive samples (e.g., blood pressure variation values); portions of the signal with a blood pressure derivative that is greater than a first threshold rate or less than a second threshold rate, possibly with a minimum range or a maximum range (e.g., a total change) and possibly for a minimum or maximum threshold time duration, or a combination of these values; a rise above a minimum threshold followed by a drop by at least the same amount in consecutive samples or over a finite time period; moving percentile windows to identify high-diastolic (or low-systolic) components; a difference between the raw blood pressure signal and the filtered signal above a certain threshold for a minimum or maximum time duration. Table I shows example characteristics and thresholds.

Table II shows other parameters for processing the raw blood pressure signal.

TABLE II

Example parameters for identifying portions of the signal

| Parameter | Example Value |
| --- | --- |
| Low-pass cutoff frequency | 20 Hertz |
| Maximum difference between raw signal and low-pass-filtered signal | 3 mmHg |
| Maximum block size for recovery of signal (interpolation of missing or excluded portions) | 10 samples |
| Identify constant signal - minimum # samples | 5 samples |
| Maximum diastolic | 130 mmHg |

Processing circuitry 110 determines a filtered signal indicative of the blood pressure of the patient by excluding the at least one first portion and the at least one second portion from the signal (1006). In some examples, processing circuitry 110 modifies an identified portion instead of excluding the identified portion. In examples in which an excluded portion is less than a maximum block size, processing circuitry 110 can recovery the signal by interpolating (e.g., linearly interpolating) the surrounding portions of the signal. Processing circuitry 110 can determine the filtered signal based on the portions of the signal that were not excluded, along with the modified portions of the signal.

Processing circuitry 110 determines a set of mean arterial pressure values based on the filtered signal (1008). Processing circuitry 110 can determine a mean arterial pressure value based on an average (e.g., a weighted average) of the systolic and diastolic values of the signal. Processing circuitry 110 then determines an autoregulation status of the patient based on the set of mean arterial pressure values (1010). Processing circuitry 110 can use the mean arterial pressure values to determine correlation coefficient values. Additional example details of using mean arterial pressure values to determine an autoregulation status may be found in commonly assigned U.S. patent application Ser. No. 15/980, 235, filed on May 15, 2018, entitled "Determining a Limit

TABLE I

Example of characteristics and thresholds to identify signal portions to exclude or to modify.

| Characteristic | Threshold | Example Value |
| --- | --- | --- |
| Blood pressure value | Maximum blood pressure value | 250 mmHg |
| Blood pressure value | Minimum blood pressure value | 10 mmHg |
| Difference in blood pressure between two consecutive portions | Blood pressure variation value (e.g., maximum jump) | 50 mmHg |
| Monotonic change | Blood pressure variation value (e.g., maximum change) | 160 mmHg |
| Difference in blood pressure between three consecutive portions | Maximum spike | 20 mmHg |
| Filtering frequency | Low-pass cutoff frequency | 20 Hertz |
| Difference between raw signal and low-pass-filtered signal | Maximum difference to filtered signal | 3 mmHg |
| Range of deviation | Predetermined range of deviation | 1 mmHg |
| Range of deviation | Minimum number of samples for constant signal | 5 samples |
| Diastolic value of signal | Blood pressure threshold value | 130 mmHg |
| Diastolic value of signal | Percentile value | $10^{th}$ percentile | of Autoregulation," the entire contents of which is incorporated herein by reference in its entirety.

Processing circuitry 110 can use a cleaning algorithm that includes identifying artifacts in the raw signal to clean the signal, identifying bypass and pulsatile portions of the signal, and calculating the mean arterial pressure values. For portions identified as pulsatile, processing circuitry 110 can calculate mean arterial pressure values using beat-to-beat information from the signal. For portions that indicate that the patient is undergoing a cardiopulmonary bypass procedure, processing circuitry 110 can calculate mean arterial pressure values using a moving average of the signal.

To determine a filtered signal, processing circuitry 110 can identify artifacts in the raw signals by identifying portions of the signal including a characteristic of the signal that exceeds a threshold. Events that can cause artifacts include electrocautery, transducer shifts, line flushing, AC interference, and probe movement. Processing circuitry 110 can identify portions of the blood pressure signal that include artifacts. Processing circuitry 110 can pass or set a corresponding flag for the identified portions. Processing circuitry 110 may activate an alarm or process a more accurate estimate of the mean arterial pressure based on the flags. For example, processing circuitry 110 can exclude or modified the flagged portions of the signal.

Processing circuitry 110 can recover a portion responsive to making a positive identification of a number of features. Processing circuitry 110 can also recursively identify new issues with the fixed signal. Processing circuitry 110 may be configured to recover a portion of the signal only under some conditions, such as when number of consecutive identified samples is above or below a threshold.

Processing circuitry 110 may be configured to detect artifacts that affect autoregulation by using a combination of parameters and characteristics along with signal processing techniques to process the raw blood pressure signal or the cleaned BP signal. These signal processing techniques can include filtering, interpolation, and detection of portions of the signal that include undesired characteristics (e.g., characteristics that exceed thresholds). Processing circuitry 110 may apply machine learning methods to evaluate the set of optimal parameters and thresholds to identify portions for cleaning. Processing circuitry 110 can calculate the characteristics and thresholds parametrically from real patient data, such as historical patient data.

Processing circuitry 110 can identify a portion of the blood pressure signal including a first derivative of the signal that is greater than a threshold for a predetermined time duration. In examples in which the first derivative of the signal exceeds the threshold may indicate a line flushing event. To detect a catheter adjustment, processing circuitry 110 can use a moving window to detect a shift of the signal immediately before and immediately after the adjustment. Processing circuitry 110 may be configured to apply, for example, a Heaviside function or some other function that can identify shifts in the blood pressure values of the signal.

In the example of FIG. 11, processing circuitry 110 receives a signal indicative of a blood pressure of a patient (1100). Processing circuitry 110 then identifies a first set of erroneous portions of the signal for exclusion (1102). Processing circuitry 110 also identifies a second set of erroneous portions of the signal for modification (1104). Although processes 1102, 1104, and 1106 are shown as occurring simultaneously, these processes may be performed iteratively in other examples. Processing circuitry 110 may identify portions of the raw arterial blood pressure signal with artifacts and clean the raw signal to conduct a beat-to-beat analysis. Processing circuitry 110 can use the beat-to-beat analysis to generate a filtered signal. Processing circuitry 110 may use a window of the blood pressure signal with a duration of ten seconds and a sampling rate of 100 hertz. Processing circuitry 110 can identify portions of the signal including a characteristic of the signal that exceeds a threshold for excluding or modifying.

For example, processing circuitry 110 can identify portions for exclusion or modification by determining that a blood pressure value is less than a minimum blood pressure value, where the minimum blood pressure value may be less than or equal to 25 mmHg. An example minimum blood pressure value is 20 mmHg. Processing circuitry 110 can identify a portion for exclusion or modification by determining that a blood pressure value is greater than a maximum blood pressure value, where the maximum blood pressure value may be greater than or equal to 200 mmHg. An example maximum blood pressure value is 250 mmHg.

Processing circuitry 110 can identify a portion for exclusion or modification by determining that a difference in blood pressure between two consecutive portions of the signal is greater than a blood pressure variation value. The blood pressure variation value may be greater than or equal to 40 mmHg, where an example blood pressure variation value is 50 mmHg. Processing circuitry 110 can identify a portion for exclusion or modification by determining that a derivative of the at least one first portion of the signal exceeds a threshold rate for longer than a threshold time duration for a total change in the signal greater than a blood pressure variation value.

Processing circuitry 110 can identify a portion for exclusion or modification by determining that an increase (or decrease) in consecutive samples of at least 20 mmHg followed by a decrease (or increase) in consecutive samples of at least 20 mmHg. Processing circuitry 110 can identify a portion for exclusion or modification by determining that at least five consecutive samples have the same value or are within a predetermined range of deviation. Processing circuitry 110 can identify a portion for exclusion or modification by determining a continuous (e.g., monotonic) increase or decrease in blood pressure values of at least 160 mmHg.

Processing circuitry 110 can identify a portion for exclusion or modification by determining a difference of at least 3 mmHg between the raw signal and a low-pass-filtered signal. Processing circuitry 110 can identify a portion for exclusion or modification by determining that the portion has a high level of noise, such a standard deviation of the derivative of the raw signal that exceeds 15 mmHg per second. Processing circuitry 110 can identify a portion for exclusion or modification by determining that the tenth percentile value of the raw signal over a one-second duration exceeds 130 mmHg. Processing circuitry 110 can identify a portion for exclusion or modification by determining that the blood pressure value continuously increases or continuously decreases for more than one second.

Processing circuitry 110 may be configured to independently tag each identified portion. After processing circuitry 110 has processed all of the rules to identify the affected samples, processing circuitry 110 can tag small regions of signal (e.g., less than one-tenth of one second) as a spike or as high-frequency noise (e.g., the second set of erroneous portions). Processing circuitry 110 may be configured to remove the second set of erroneous portions. Processing circuitry 110 can then replace the second set of erroneous portions with cleaned portions (1106). The cleaned portions may be linearly interpolated from the blood pressure values surrounding the tagged portion. Processing circuitry 110 may replace an identified portion of the blood pressure signal with an interpolated portion, where the identified portion is less than threshold time duration, such as 0.1, 0.2, 0.5, or 1.0 seconds. Thus, processing circuitry 110 can recover the second set of erroneous portions that might have been corrupted.

Processing circuitry 110 determines the union of all erroneous portions of the signal (1108). Processing circuitry 110 can then exclude the erroneous portions of the signal that still include a characteristic that exceed a threshold (1110). Processing circuitry 110 may identify and exclude isolated, untagged portions of the signal that span less than one second. Processing circuitry 110 can generate the filtered signal based on the remaining portions and the cleaned portions of the signal (1112).

Figure 12:
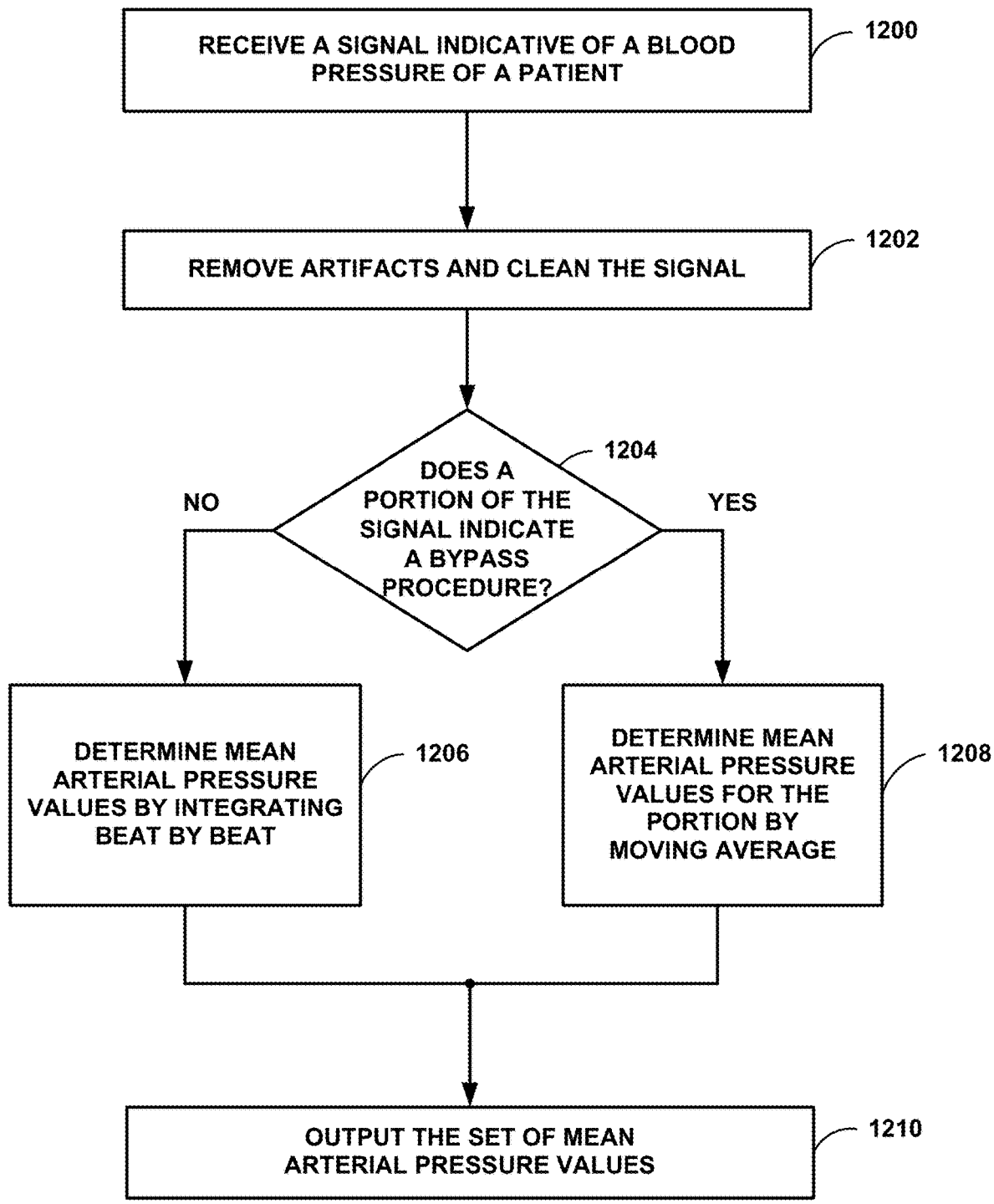

In the example of FIG. 12, processing circuitry 110 receives a signal indicative of a blood pressure of a patient (1200). Processing circuitry 110 then removes artifacts to clean the signal (1202). Processing circuitry 110 can remove artifacts by identifying portions that include a characteristic that exceeds a threshold. Processing circuitry 110 can also determine whether a portion of the signal indicates a cardiopulmonary bypass procedure (1204). Given a window of ten seconds of the signal, processing circuitry 110 classifies the window as indicating a bypass procedure, according to the prediction parameters, which may be calculated from training data.

Responsive to determining that the portion of the signal does not indicate the cardiopulmonary bypass procedure, processing circuitry 110 determines mean arterial pressure values for the portion by integrating the blood pressure values beat by beat (1206). The beat by beat integration may include a weighted average of the systolic and diastolic blood pressure values of the signal, or any other beat by beat method of determining a mean arterial pressure value. Responsive to determining that the portion of the signal indicates the cardiopulmonary bypass procedure, processing circuitry 110 determines mean arterial pressure values for the portion based on a moving average of the blood pressure values of the raw signal (1208). The moving average may include an average of the samples across a five- or ten-second window. Processing circuitry 110 then outputs the set of mean arterial pressure values, for example, for presentation via a display (1210).

Figure 13:
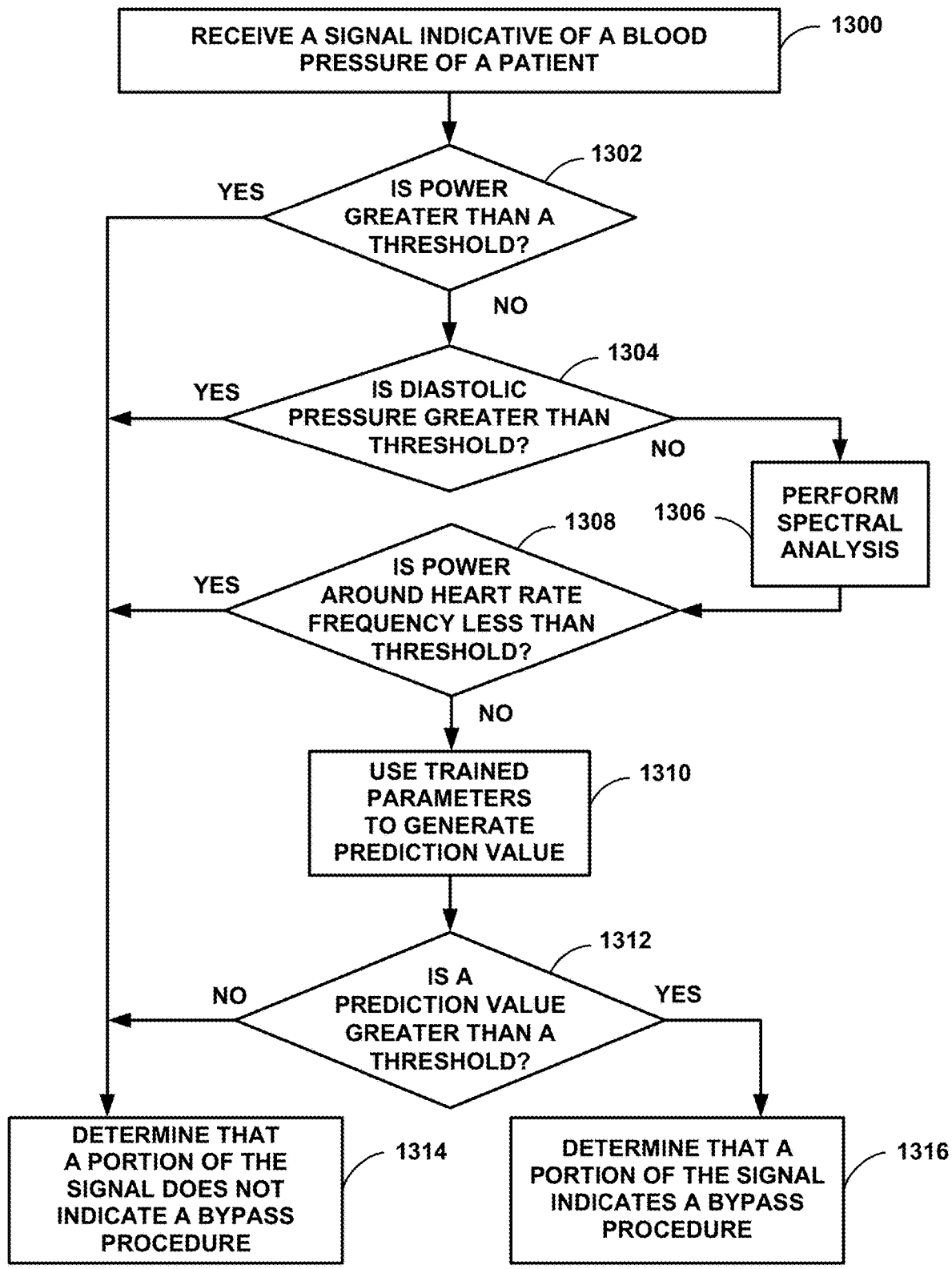

FIG. 13 shows an example process for identifying a portion of a blood pressure signal as indicating a cardiopulmonary bypass procedure. Thus, processing circuitry 110 can use the example process shown in FIG. 13 to perform step 1204 shown in FIG. 12. In the example of FIG. 13, processing circuitry 110 receives a signal indicative of a blood pressure of a patient (1300). Processing circuitry 110 can calculate a power spectrum of the signal, which may be computationally expensive. Thus, as initial conditions, processing circuitry 110 can check some initial conditions to avoid the processing-intensive task of calculating the power spectrum. Processing circuitry 110 may determine whether the power of the signal is greater than a threshold (1302). For example, processing circuitry 110 can determine whether the square root of the mean power of the signal is larger than 50.0 arbitrary units (a.u.). Responsive to determining that the power of the signal is greater than the threshold, processing circuitry 110 determines that the portion of the signal does not indicate a cardiopulmonary bypass procedure (1314).

Processing circuitry 110 can also determine whether the diastolic pressure of the signal is greater than a threshold (1304). For example, processing circuitry 110 may determine whether the absolute diastolic value, which may be defined as the fifth percentile of the unfiltered raw signal window, is greater than 110 mmHg. Responsive to determining that the diastolic pressure of the signal is greater than the threshold, processing circuitry 110 determines that the portion of the signal does not indicate a cardiopulmonary bypass procedure.

If neither of these steps indicates a cardiopulmonary bypass procedure, processing circuitry 110 performs a spectral analysis of the signal (1306) and determines whether the power around the heart rate frequency is less than a threshold (1308). For example, processing circuitry 110 can determine whether the total power in a frequency band around the estimated heart rate frequency is larger than 9.0 a.u. Processing circuitry 110 can also determine whether the estimated heart rate is less than a predetermined heart rate, such as 90 beats per minutes. Responsive to determining that the power around the heart rate frequency is less than the threshold and the estimated heart rate is less than the predetermined heart rate.

If none of the above conditions are met, processing circuitry 110 may use trained parameters to generate a prediction value (1310). For example, processing circuitry 110 can calculate a set of features for the prediction value. Processing circuitry 110 can classify a window as indicating a bypass procedure responsive to determining that the prediction value is greater than 0.5. Processing circuitry 110 can classify a window as not indicating the bypass procedure responsive to determining that the prediction value is less than 0.5.

Processing circuitry 110 can calculate the parameters for determining the prediction value based on a machine learning approach (e.g., logistic regression) using several features of the blood pressure signals. Examples of the features that processing circuitry 110 can use are power, diastolic pressure, heart rate, and frequencies derived from a power analysis. The prediction value is a single number calculated by processing circuitry 110 by combining these features in a predetermined equation that uses the trained parameters. The trained parameters are the result of processing circuitry 110 training the algorithms described herein. Processing circuitry 110 can classify a portion of the signal as indicating a cardiopulmonary bypass procedure according to the prediction value.

For example, processing circuitry 110 can classify a portion as indicating a cardiopulmonary bypass procedure if the prediction value is greater than 0.5 and classify the portion as non-bypass if the prediction value is not greater than 0.5. Processing circuitry 110 can use the machine learning training to determine a parameter for the feature "HR" (e.g., heart rate) equal to 0.15 and a parameter for the feature "power" equal to 0.5. Processing circuitry 110 can use Equation (1) to calculate the prediction value. Equation (1) has only two features, but processing circuitry 110 can use more than two features in some examples.

$$\text{Prediction value} = 0.15 \times \text{HR}_{current} + 0.5 \times \text{power}_{current} \quad (1)$$

Figure 14:
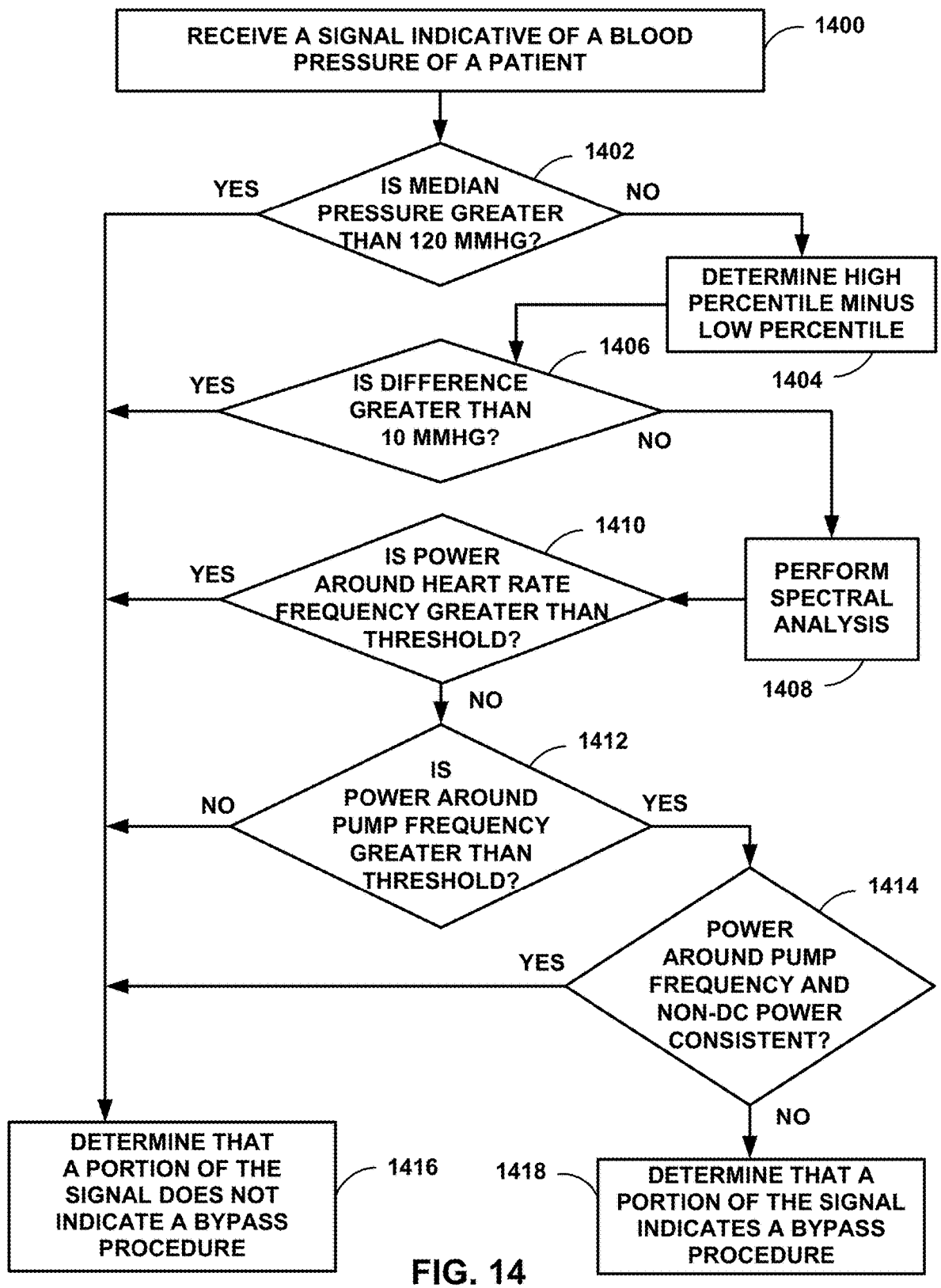

FIG. 14 shows an example process for identifying a portion of a blood pressure signal as indicating a cardiopulmonary bypass procedure. Thus, processing circuitry 110 can use the example process shown in FIG. 14 to perform step 1204 shown in FIG. 12. FIG. 14 shows another example process for determining whether a portion of a blood pressure signal indicates a cardiopulmonary bypass procedure. In the example of FIG. 14, processing circuitry 110 receives a signal indicative of a blood pressure of a patient (1400). Processing circuitry 110 then determines whether the median pressure of a portion of the signal is greater than 120 mmHg (1402). Responsive to determining that the median pressure of a portion of the signal is greater than 120 mmHg, processing circuitry 110 determines that the portion of the signal does not indicate a cardiopulmonary bypass procedure (1416).

Responsive to determining that the median pressure of a portion of the signal is not greater than 120 mmHg, processing circuitry determines a high percentile value minus a low percentile value (1404). For example, processing circuitry 110 can subtract the fifth percentile value from the 95th percentile value. Responsive to determining that the difference is greater than ten mmHg, processing circuitry 110 determines that the portion of the signal does not indicate a cardiopulmonary bypass procedure (1416). Responsive to determining that the difference is not greater than ten mmHg, processing circuitry 110 performs a spectral analysis of the signal (1408).

Processing circuitry 110 then determines whether the power around the heart rate frequency is greater than a threshold (1410). For example, processing circuitry 110 can determine whether the power in a frequency band between 0.5 and 2.0 hertz is greater than 2 a.u. Responsive to determining that the power around the heart rate frequency is greater than the threshold, processing circuitry 110 determines that the portion of the signal does not indicate a cardiopulmonary bypass procedure. Responsive to determining that the power around the heart rate frequency is not greater than the threshold, processing circuitry 110 determines whether the power around the pump frequency is greater than a threshold (1412). For example, processing circuitry 110 can determine whether the power in a frequency band between two and five hertz is greater than one a.u. Responsive to determining that the power around the pump frequency is not greater than the threshold, processing circuitry 110 determines that the portion of the signal does not indicate a cardiopulmonary bypass procedure.

Responsive to determining that the power around the pump frequency is greater than the threshold, processing circuitry 110 determines whether the power around the pump frequency and the non-direct-current power are consistent (1414). Responsive to determining that the power around the pump frequency and the non-direct-current power are consistent, processing circuitry 110 determines that the portion of the signal does not indicate a cardiopulmonary bypass procedure. Responsive to determining that the power around the pump frequency and the non-direct-current power are not consistent, processing circuitry 110 determines that the portion of the signal indicates a cardiopulmonary bypass procedure (1418).

Processing circuitry 110 can detect portions indicating a cardiopulmonary bypass procedure by using a specific kernel or combination of kernels to enhance bypass characteristics. Processing circuitry 110 can classify the portion as bypass or non-bypass by using the kernel(s) to detect frequencies around the bypass pump frequency. Processing circuitry 110 can identify samples above a threshold to exclude portions of the signal that may not belong to bypass. Processing circuitry 110 may calculate the amplitude of oscillations, or an interpercentile difference, to classify the portion of signal as bypass or not bypass. Processing circuitry 110 can perform a power analysis of the signal via a Fourier Transform or a Least-Square Spectral Analysis around specified frequencies such as the expected heart-rate frequency and/or expected bypass pump frequency. Processing circuitry 110 can use the power analysis to detect lack of heartbeat and existence of a bypass pump. Processing circuitry 110 may use a combination of thresholds to evaluate the power around each frequency to classify the portion as indicating bypass or non-bypass.

In some examples, processing circuitry 110 can post-process the bypass classifier output by setting the bypass flag for some time period before processing circuitry 110 declares that a portion of the signal indicates bypass in order to reduce the number of false positives. Sometimes, bypass periods can show small amplitude pulsation caused by the bypass pump mechanism. These pump-induced oscillations may vary, with different frequencies and different amplitudes. Processing circuitry 110 may calculate and/or display the autoregulation status only during bypass or only during non-bypass.

Processing circuitry 110 can use the bypass algorithm describe herein along with any method for determining the autoregulation status of a patient. In addition, processing circuitry 110 can use the bypass algorithm describe herein along with any method for determining a set of mean arterial pressure values.

Responsive to determining that a portion of the signal indicates a cardiopulmonary bypass procedure, processing circuitry 110, processing circuitry 110 can apply a moving average with a duration of one second to the elements in the ten-second window in steps of 0.5 seconds. Processing circuitry 110 can calculate the diastolic and systolic values during a bypass procedure as the 5th and 95th percentile values of the same one-second moving window. In examples in which the one-second moving window contains invalid samples, processing circuitry 110 performs the calculations on the available valid samples. In examples in which all the samples in one-second window are invalid, the calculation for that period will trigger a flag indicating an invalid mean arterial pressure value. Processing circuitry 110 may identify the heart-rate during this portion of the signal as not available. Processing circuitry 110 can associate a bypass flag with each of half-second steps.

Figure 15:
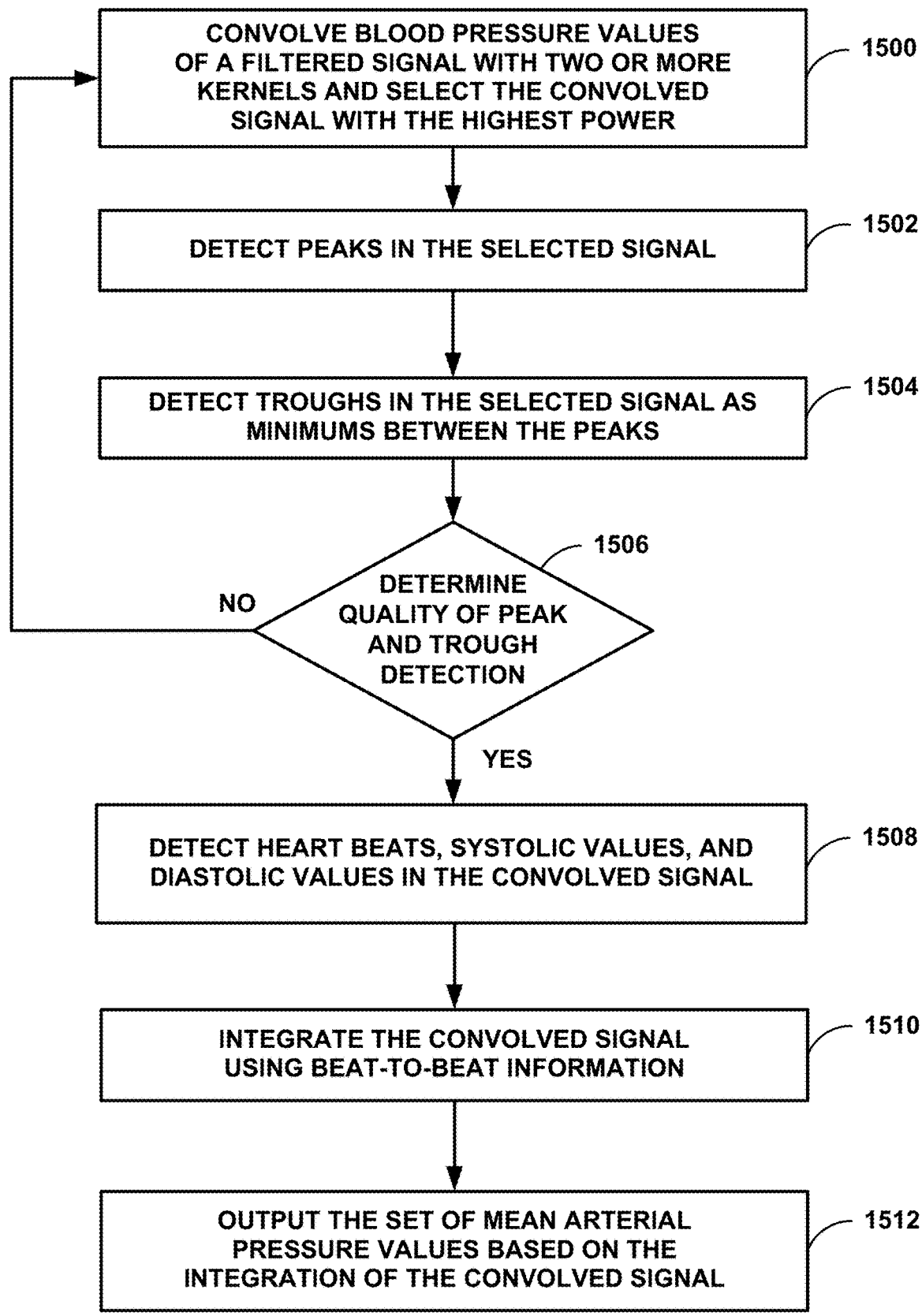

FIG. 15 shows an example process for determining mean arterial pressure values by convolving a blood pressure signal with one or more kernels. Processing circuitry 110 can use a kernel to identify systolic peaks, diastolic troughs, and heart beats from the blood pressure signal. Processing circuitry 110 can use the peaks, troughs, and heart beats in the determination of mean arterial pressure values. In the example of FIG. 15, processing circuitry 110 convolves blood pressure values of a filtered signal with two or more kernels and selects the convolved signal with the highest power (1500). For example, processing circuitry 110 can perform a convolution of the cleaned signal with six different kernels, where each kernel enhances beat characteristics at different frequencies. The frequencies may be 0.75, 1.0, 1.25, 1.5, 2.0, and 2.5 hertz. These frequencies may represent the range of frequencies seen in training data, and are able to capture the expected range of frequencies expected in human population, which is 30 to 240 beats per minutes. Processing circuitry 110 can use kernels with zero-mean and a total power that is normalized to one. After processing circuitry 110 applies each kernel to the filtered signal, processing circuitry 110 calculates the square root of the average power of the kernel-filtered signals (e.g., the convolved signals). Processing circuitry 110 may then select the convolved signal with the highest power for further analysis.

In the example of FIG. 15, processing circuitry 110 detects peaks in the selected signal (1502). Processing circuitry 110 can also detect troughs in the selected signal as the minimums between the peaks (1504). Processing circuitry 110 can apply a peak detection algorithm to the selected filtered signal. Processing circuitry 110 may initially apply a very strict criteria to detect peaks. Processing circuitry 110 may then determine the quality of the peak and trough detection (1506).

Responsive to determining that the signal does not have a high quality level, processing circuitry 110 can convolve the filtered signal with additional kernels or select a different convolved signal of the six convolved signals. Processing circuitry 110 may also reattempt peak detection if the signal did not pass the strict criteria for peak detection. Processing circuitry 110 can check if there is a more suitable filtering to use in the window of the blood pressure signal. Processing circuitry 110 may re-estimate the heartrate using spectral analysis and use less conservative parameters for peak detection. In this way, processing circuitry 110 can detect less conventional waveforms, for example the waveforms that occur in arrythmia, or the waveforms that occur when a precocious ventricular ejection occurs.

In some examples, the signal may pass this strict criteria and processing circuitry 110 can determine the signal has very good quality, which may mean no missing peaks and consistent interpeak distance and peak heights. Responsive to determining that the signal has a high quality level, processing circuitry 110 may determine that the detected peaks are a good estimate for the systolic peaks in the blood pressure signal. Processing circuitry 110 may then detect heart beats, systolic values, and diastolic values in the selected signal (1508). Processing circuitry 110 can perform a lookup for the blood pressure systolic peaks on the original (e.g., unfiltered) signal. Processing circuitry 110 may identify the diastolic values as the minimum of the sample points between each peak.

Once the peaks and troughs have been identified in the ABP signal, processing circuitry 110 can perform a final check on the beat quality by looking at the median of beat duration and the median distance or time to the median. Processing circuitry 110 can flag a beat as invalid if the beat falls outside the criteria established for the beat quality, such as a duration between 0.1 and 2.0 seconds, having a duration that is less than 150% of the median beat duration, and valid sample values. Processing circuitry 110 may integrate the convolved signal using beat-to-beat information (1510). Processing circuitry 110 can calculate mean arterial pressure values by integrating the samples that constitute the beat. This integration can generate a more accurate value for mean arterial pressure than simply finding the mean of the samples that constitute the beat. Performing a simple average can sometimes introduce an error in mean arterial pressure that is a function of the heart rate. This can be significant for sufficiently high heart rates.

Processing circuitry 110 can define a time stamp for each beat as the middle point between both diastolic troughs. Processing circuitry 110 may define the beginning and ending of each beat as the diastolic troughs. Processing circuitry 110 may be configured to calculate the diastolic value associated with each beat as the mean of the start and end points that define the beat. Processing circuitry 110 can also calculate the systolic value associated with the beat during the peak detection step. Processing circuitry 110 can calculate the heart rate associated with the beat as the inverse of the beat duration. In examples in which an error occurs during the processing of the beat, processing circuitry 110 may return an associated flag. Processing circuitry 110 may then output the set of mean arterial pressure values based on the integration of the convolved signal (1512).

Figure 16:
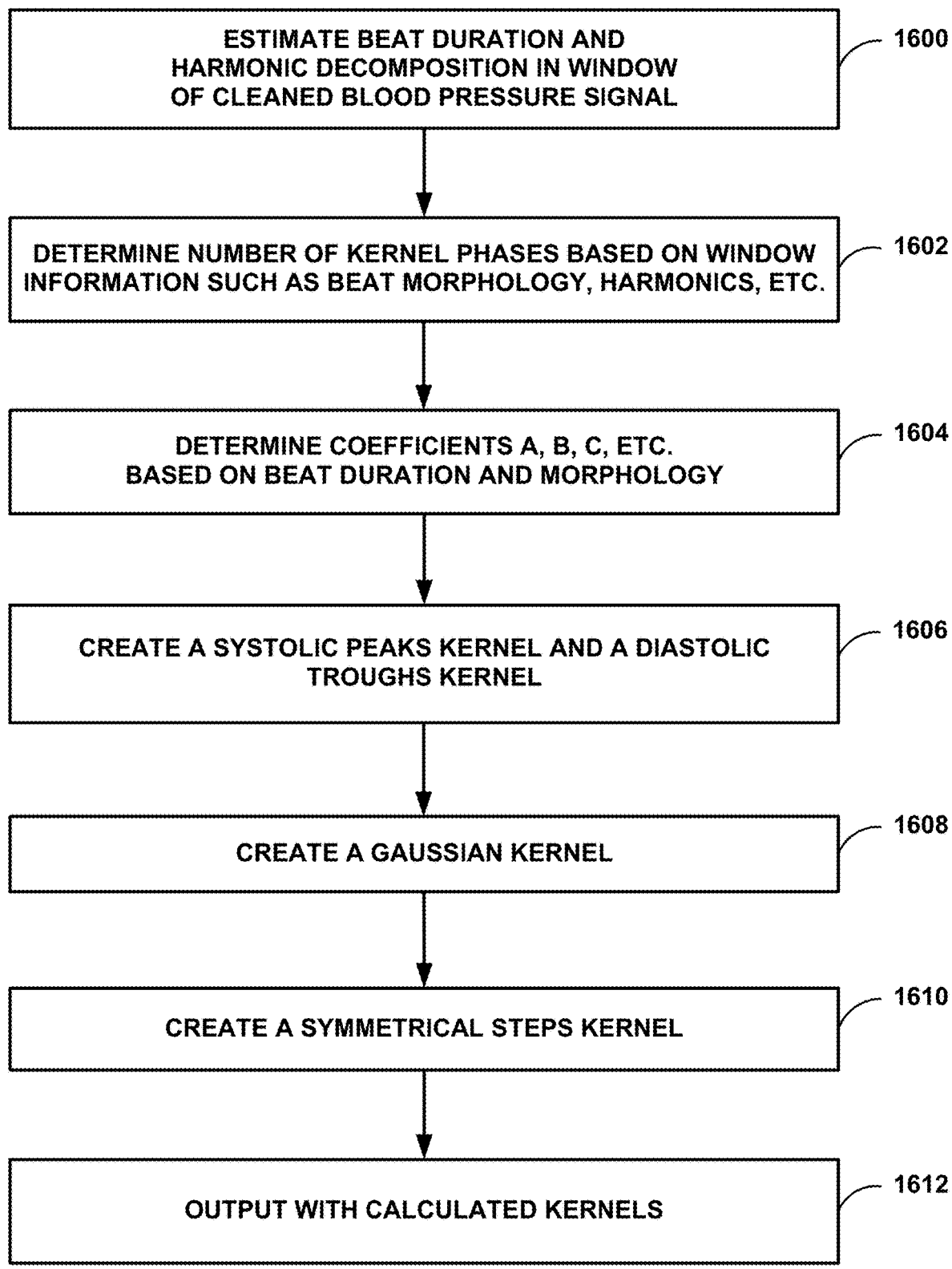

FIG. 16 shows an example process for determining mean arterial pressure values by convolving a blood pressure signal with specialized kernels. Processing circuitry 110 can use each kernel to identify one or more parameters such as systolic peaks, diastolic troughs, and heart beats from the blood pressure signal. Processing circuitry 110 can use the peaks, troughs, and heart beats in the determination of mean arterial pressure values. FIG. 16 shows an example process for using dynamic kernels to enhance or mitigate unusual beat morphologies. In the example of FIG. 16, processing circuitry 110 estimates beat duration and harmonic decomposition in a window of the cleaned blood pressure signal (1600). The harmonic decomposition may include a power spectral analysis and/or a frequency analysis. Processing circuitry 110 then determines a number of kernel phases based on window information such as beat morphology, harmonics, and other information (1602). One or more of the kernels may include a plateau, upslope, plateau, downslope and plateau (see, e.g., the kernels shown in FIGS. 9A-9D). Processing circuitry 110 determines multiple coefficients based on the beat duration and morphology (1604).

Figure 9A:
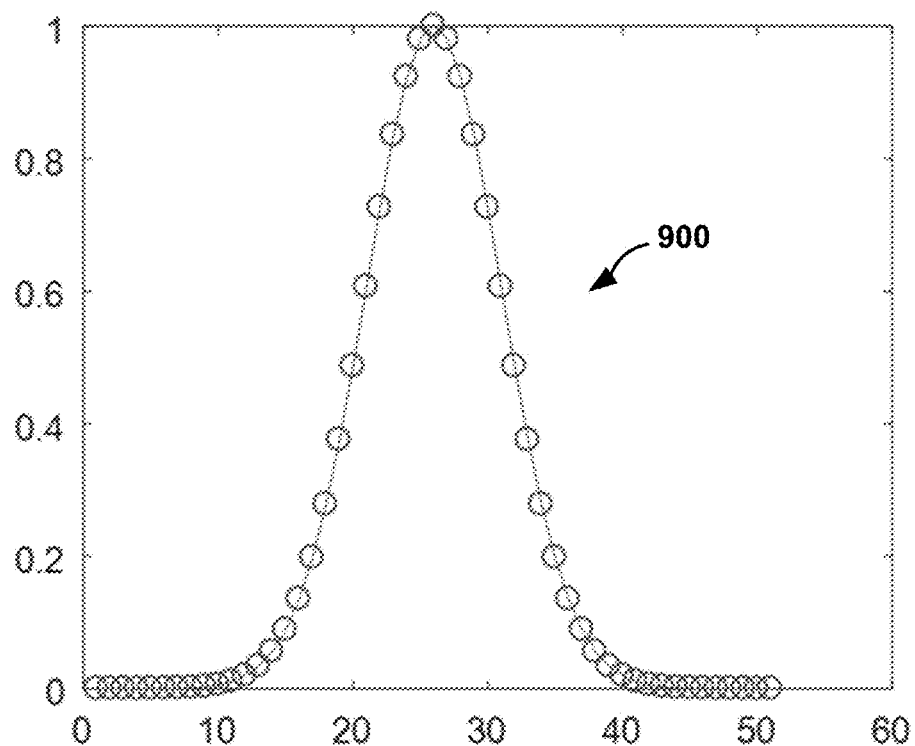
FIGS. 9A, 9B, 9C, and 9D are graphs illustrating example kernels.
Figure 9B:
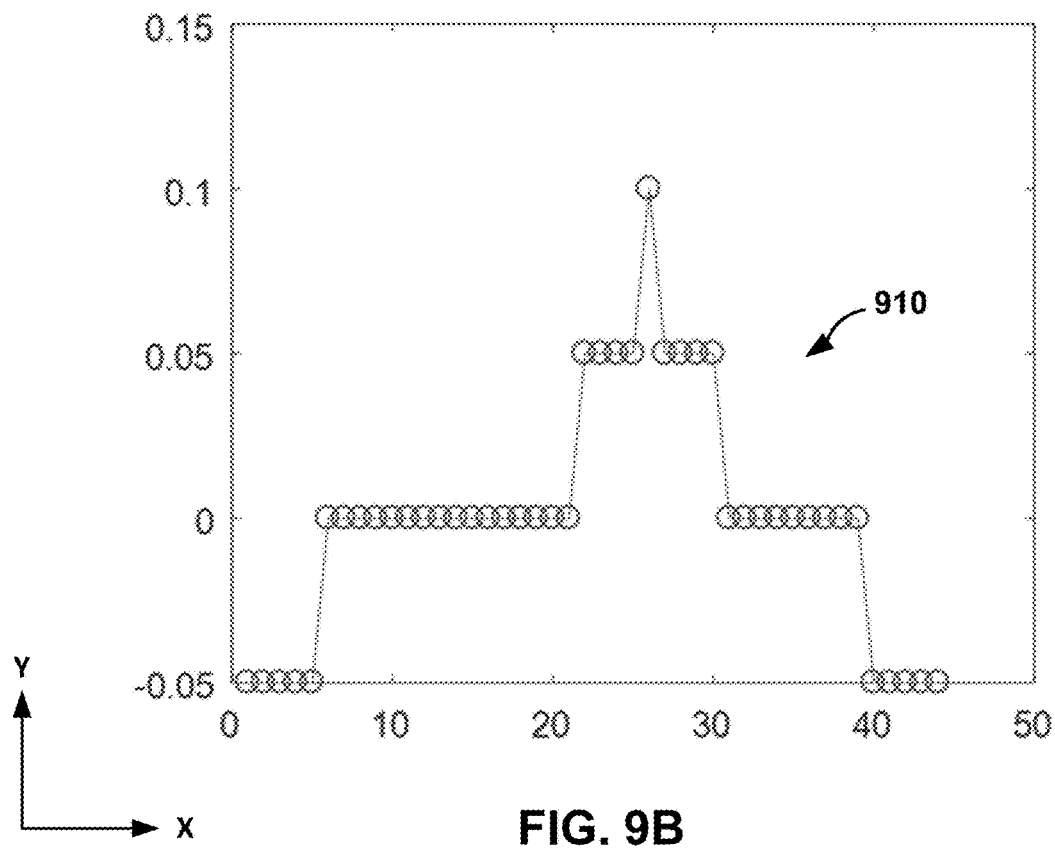
Figure 9C:
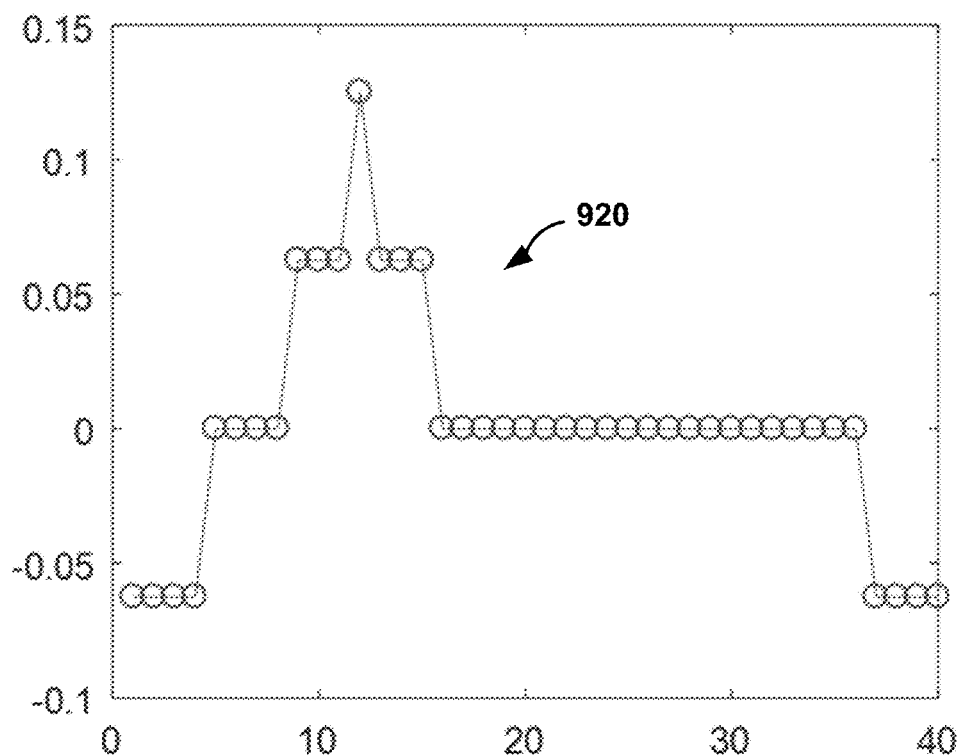
Figure 9D:
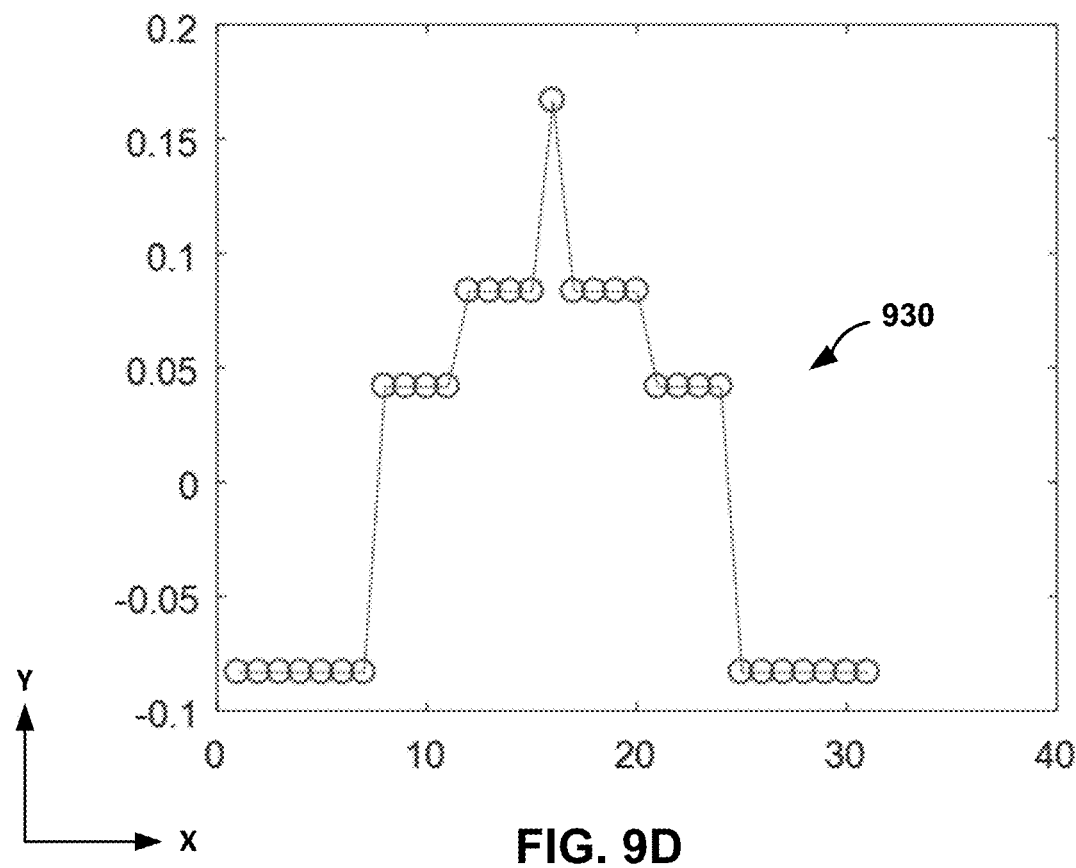

Processing circuitry 110 may create a systolic peaks kernel for detecting systolic peaks and a diastolic troughs kernel for detecting diastolic troughs (1606). Processing circuitry 110 can also create a Gaussian kernel (1608) and a symmetrical steps kernel (1610). FIG. 9A shows an example of a Gaussian kernel, FIG. 9D shows an example of a symmetrical steps kernel. Processing circuitry 110 may be configured to convolve the filtered signal with the kernels to generate convolved signals. Processing circuitry 110 may then output the convolved signals with the calculated kernels (1612). The output may also include mean arterial pressure values determined by processing circuitry 110 using the kernels.

As processing circuitry 110 receives a stream of the blood pressure signal from sensing circuitry 141, processing circuitry 110 can process the results in a pulsatile (e.g., non-bypass) mode or in a bypass mode, which may use a one-second moving average. Processing circuitry 110 can record and combine mean arterial pressure values for the last ten seconds of data. There is an overlap in the moving ten-second window, such that processing circuitry 110 may update only the mean arterial pressure values with timestamps that occur after the last valid calculated value. Using this technique, processing circuitry 110 can avoid updating older values in the buffer with more recent mean arterial pressure values due to the overlap. Thus, previous calculated values may not change during the updating process.

Processing circuitry 110 can output the raw beat-to-beat calculations and bypass calculations. Each beat-to-beat calculation may be associated with a timestamp and with corresponding flags. Processing circuitry 110 can average the available mean arterial pressure values from the last ten seconds, both from pulsatile calculations and bypass calculations. Processing circuitry 110 can average each mean arterial pressure value with a weight proportional to the duration of the mean arterial pressure value. By weighting the mean arterial pressure values, processing circuitry 110 may avoid overrepresenting short beats. Processing circuitry 110 can perform this calculation every second (e.g., one hertz). Processing circuitry 110 can output this calculation as the final mean arterial pressure output. The final output may include the ten-second average from mean arterial pressure. Correspondingly, the diastolic and systolic values are also output, as well as a flag values associated with each window.

The following numbered examples demonstrate one or more aspects of the disclosure.

Clause 1: In some examples, a device includes processing circuitry configured to receive a signal indicative of a blood pressure of the patient and identify at least one first portion of the signal including a first characteristic of the signal exceeding a first threshold. The processing circuitry is also configured to identify at least one second portion of the signal including a second characteristic of the signal exceeding a second threshold, the first characteristic being different than the second characteristic. The processing circuitry is further configured to determine a filtered signal indicative of the blood pressure of the patient by excluding the at least one first portion and the at least one second portion from the signal. The processing circuitry is configured to determine a set of mean arterial pressure values based on the filtered signal and determine an autoregulation status of the patient based on the set of mean arterial pressure values.

Clause 2: In some examples of clause 1, the device further includes sensing circuitry configured to generate a signal indicative of a blood pressure of a patient.

Clause 3: In some examples of clause 1 or clause 2, the first characteristic includes a blood pressure value.

Clause 4: In some examples of any of clauses 1-3, the processing circuitry is configured to identify the at least one first portion of the signal at least in part by determining that the first characteristic is one of less than a minimum blood pressure value or greater than a maximum blood pressure value.

Clause 5: In some examples of any of clauses 1-4, the processing circuitry is configured to determine that the first characteristic is less than the minimum blood pressure value at least in part by determining that the blood pressure value of the patient is less than twenty millimeters of mercury.

Clause 6: In some examples of any of clauses 1-5, the minimum blood pressure value is less than or equal to twenty-five millimeters of mercury.

Clause 7: In some examples of any of clauses 1-6, the processing circuitry is configured to determine that the first characteristic is greater than the maximum blood pressure value at least in part by determining that the blood pressure value is greater than two hundred and fifty millimeters of mercury.

Clause 8: In some examples of any of clauses 1-7, the maximum blood pressure value is greater than or equal to two hundred millimeters of mercury.

Clause 9: In some examples of any of clauses 1-8, the processing circuitry is configured to identify the at least one first portion of the signal at least in part by determining that a difference in blood pressure between two consecutive portions of the signal is greater than a blood pressure variation value.

Clause 10: In some examples of any of clauses 1-9, the processing circuitry is configured to determine that the difference in blood pressure between the two consecutive portions is greater than the blood pressure variation value at least in part by determining that the difference in blood pressure between the two consecutive portions is greater than fifty millimeters of mercury.

Clause 11: In some examples of any of clauses 1-10, the blood pressure variation value is greater than or equal to forty millimeters of mercury.

Clause 12: In some examples of any of clauses 1-11, the processing circuitry is configured to identify the at least one first portion of the signal at least in part by determining that a derivative of the signal exceeds a threshold rate for longer than a threshold time duration for a total change in the signal greater than a blood pressure variation value.

Clause 13: In some examples of any of clauses 1-12, the processing circuitry is configured to determine that the derivative of the at least one first portion of the signal exceeds the threshold rate for longer than the threshold time duration for a total change greater than the blood pressure variation value at least in part by determining that the derivative of the at least one first portion of the signal is greater than negative ten millimeters of mercury per second for longer than the threshold time duration for the total change greater than the blood pressure variation value.

Clause 14: In some examples of any of clauses 1-13, the threshold rate is greater than or equal to negative fifteen millimeters of mercury per second.

Clause 15: In some examples of any of clauses 1-14, the processing circuitry is configured to determine that the derivative of the at least one first portion of the signal exceeds the threshold rate for longer than the threshold time duration for a total change greater than the blood pressure variation value at least in part by determining that the derivative of the at least one first portion of the signal is less than positive ten millimeters of mercury per second for longer than the threshold time duration for the total change greater than the blood pressure variation value.

Clause 16: In some examples of any of clauses 1-15, the threshold rate is less than or equal to positive fifteen millimeters of mercury per second.

Clause 17: In some examples of any of clauses 1-16, the processing circuitry is configured to determine that the derivative of the at least one first portion of the signal exceeds the threshold rate for longer than the threshold time duration for a total change greater than the blood pressure variation value at least in part by determining that the derivative of the at least one first portion of the signal exceeds the threshold rate for longer than one second for the total change greater than the blood pressure variation value.

Clause 18: In some examples of any of clauses 1-17, the threshold time duration is greater than or equal to five hundred milliseconds.

Clause 19: In some examples of any of clauses 1-18, the processing circuitry is configured to determine that the derivative of the at least one first portion of the signal exceeds the threshold rate for longer than the threshold time duration for a total change greater than the blood pressure variation value at least in part by determining that the derivative of the at least one first portion of the signal exceeds the threshold rate for longer than the threshold time duration for the total change greater than twenty millimeters of mercury.

Clause 20: In some examples of any of clauses 1-19, the blood pressure variation value is greater than or equal to fifteen millimeters of mercury.

Clause 21: In some examples of any of clauses 1-20, the processing circuitry is configured to identify the at least one first portion of the signal at least in part by determining that a number of consecutive samples of the blood pressure of the patient are within a predetermined range of deviation.

Clause 22A: In some examples of any of clauses 1-21, the processing circuitry is configured to determine that the number of consecutive samples are within the predetermined range of variation at least in part by determining that five consecutive samples are within a range of variation of one millimeter of mercury.

Clause 22B: In some examples of any of clauses 1-22A, the predetermined range of variation is less than or equal to two millimeters of mercury.

Clause 23: In some examples of any of clauses 1-22B, the processing circuitry is configured to identify the at least one first portion of the signal at least in part by determining that a monotonic change in the blood pressure of the patient of the signal is greater than a blood pressure variation value.

Clause 24: In some examples of any of clauses 1-23, the processing circuitry is configured to determine that the monotonic change is greater than a blood pressure variation value at least in part by determining that the monotonic change is greater than one hundred and sixty millimeters of mercury.

Clause 25: In some examples of any of clauses 1-24, the blood pressure variation value is greater than or equal to one hundred and forty millimeters of mercury.

Clause 26: In some examples of any of clauses 1-25, the processing circuitry is configured to identify the at least one first portion at least in part by determining that the monotonic change occurs for more than one second.

Clause 27: In some examples of any of clauses 1-26, the processing circuitry is configured to identify the at least one first portion at least in part by determining that the monotonic change occurs for more than a threshold time duration, where the threshold time duration is greater than or equal to eight hundred milliseconds.

Clause 28: In some examples of any of clauses 1-27, the processing circuitry is configured to identify the at least one first portion of the signal at least in part by determining that a level of noise of the signal is greater than the first threshold level.

Clause 29: In some examples of any of clauses 1-28, the processing circuitry is configured to determine that the level of noise of the signal is greater than the first threshold level at least in part by determining that a standard deviation of a derivative of the signal is greater than fifteen millimeters of mercury per second.

Clause 30: In some examples of any of clauses 1-29, the processing circuitry is configured to determine that the level of noise of the signal is greater than the first threshold level at least in part by determining that a standard deviation of a derivative of the signal is greater than a threshold rate, where the threshold rate is greater than or equal to twelve millimeters of mercury per second.

Clause 31: In some examples of any of clauses 1-30, the processing circuitry is configured to identify the at least one first portion of the signal at least in part by determining that a diastolic value of the signal is greater than a blood pressure threshold value.

Clause 32: In some examples of any of clauses 1-31, the processing circuitry is configured to determine that the diastolic value is greater than the blood pressure threshold value at least in part by determining that the diastolic value of the signal is greater than one hundred and thirty millimeters of mercury.

Clause 33: In some examples of any of clauses 1-32, the blood pressure threshold value is greater than or equal to one hundred and twenty millimeters of mercury.

Clause 34: In some examples of any of clauses 1-33, the processing circuitry is configured to determine that the diastolic value within the first portion is greater than the blood pressure threshold value at least in part by determining that a percentile value is greater than the blood pressure threshold value.

Clause 35: In some examples of any of clauses 1-34, the percentile value is a tenth percentile of the signal.

Clause 36: In some examples of any of clauses 1-35, the percentile value is less than or equal to a fifteenth percentile of the signal.

Clause 37: In some examples of any of clauses 1-36, the processing circuitry is configured to identify the at least one first portion at least in part by determining that a diastolic value of the signal is greater than a blood pressure threshold value for a threshold time duration.

Clause 38: In some examples of any of clauses 1-37, the threshold time duration is less than or equal to two seconds.

Clause 39: In some examples of any of clauses 1-38, the processing circuitry is further configured to identify at least one third portion of the signal including a third characteristic of the signal exceeding a third threshold.

Clause 40: In some examples of any of clauses 1-39, the processing circuitry is configured to determine the filtered signal at least in part by modifying the at least one third portion of the signal.

Clause 41: In some examples of any of clauses 1-40, the processing circuitry is configured to identify the at least one third portion at least in part by determining that a difference in blood pressure between a first consecutive portion of the signal and a second consecutive portion of the signal is greater than a first blood pressure variation value and determining that a difference in blood pressure between the second consecutive portion of the signal and a third consecutive portion of the signal is greater than a second blood pressure variation value.

Clause 42: In some examples of any of clauses 1-41, the processing circuitry is configured to determine that the first sample is greater than the second sample by at least the first blood pressure threshold value at least in part by determining that the first sample is greater than the second sample by at least twenty millimeters of mercury, and the processing circuitry is configured to determine that the second sample is greater than the third sample by at least the second blood pressure threshold value at least in part by determining that the second sample is greater than the third sample by at least twenty millimeters of mercury.

Clause 43: In some examples of any of clauses 1-42, the processing circuitry is configured to modify the at least one third portion of the signal at least in part by setting the second consecutive portion of the signal to a modified value. A difference between the modified value and a value the first consecutive portion of the signal is less than a difference between the modified value and a value the second consecutive portion of the signal. A difference between the modified value and a value the third consecutive portion of the signal is less than the difference between the modified value and the value the second consecutive portion of the signal.

Clause 44: In some examples of any of clauses 1-43, the processing circuitry is configured to modify the at least one third portion of the signal at least in part by setting the second consecutive portion of the signal to a mean or a median of a value the first consecutive portion of the signal and a value the third consecutive portion of the signal.

Clause 45: In some examples of any of clauses 1-44, the processing circuitry is configured to identify the at least one third portion at least in part by determining a low-pass-filtered signal from the at least one third portion of the signal and determining that a difference between a blood pressure value of the at least one third portion of the signal and an associated blood pressure value of low-pass-filtered signal is greater than a blood pressure variation value.

Clause 46: In some examples of any of clauses 1-45, the processing circuitry is configured to determine the low-pass-filtered signal at least in part by low-pass filtering the signal using a cutoff frequency of between approximately ten hertz and approximately thirty hertz.

Clause 47: In some examples of any of clauses 1-46, the processing circuitry is configured to determine that the difference between the blood pressure value of the at least one third portion of the signal and the associated blood pressure value is greater than the blood pressure variation value at least in part by determining that the difference between the blood pressure value of the at least one third portion of the signal and the associated blood pressure value is greater than three millimeters of mercury.

Clause 48: In some examples of any of clauses 1-47, the blood pressure variation value is greater than or equal to two millimeters of mercury.

Clause 49: In some examples of any of clauses 1-48, the processing circuitry is configured to identify the at least one third portion at least in part by determining that the signal has an invalid value within the at least one third portion for less than a threshold time duration.

Clause 50: In some examples of any of clauses 1-49, the threshold time duration is less than or equal to one second.

Clause 51: In some examples of any of clauses 1-50, the processing circuitry is configured to identify the at least one third portion at least in part by determining that the third characteristic of the signal exceeds the third threshold for less than a threshold time duration.

Clause 52: In some examples of any of clauses 1-51, the threshold time duration is less than or equal to one second.

Clause 53: In some examples of any of clauses 1-52, the processing circuitry is configured to identify at least one fourth portion of the signal including a fourth characteristic of the signal indicates that the patient is undergoing a cardiopulmonary bypass procedure. The processing circuitry is also configured to determine a subset of the set of mean arterial pressure values for the at least one fourth portion based on a moving average of the signal in response to determining that the fourth characteristic of the signal indicates that the patient is undergoing the cardiopulmonary bypass procedure.

Clause 54: In some examples of any of clauses 1-53, the processing circuitry is configured to identify the at least one fourth portion at least in part by determining that a mean power of the signal is less than a threshold power level.

Clause 55: In some examples of any of clauses 1-54, the processing circuitry is configured to identify the at least one fourth portion at least in part by determining that a diastolic value of the signal is less than a blood pressure threshold value.

Clause 56: In some examples of any of clauses 1-55, the processing circuitry is configured to determine that the diastolic value is less than the blood pressure threshold value at least in part by determining that a percentile value is less than the blood pressure threshold value, where the percentile value is less than or equal to a fifteenth percentile of the signal.

Clause 57: In some examples of any of clauses 1-56, the processing circuitry is configured to identify the at least one fourth portion at least in part by determining that a total power within a frequency band is less than a threshold power level, the frequency band including an estimated heart rate frequency of the patient.

Clause 58: In some examples of any of clauses 1-57, the processing circuitry is configured to identify the at least one fourth portion at least in part by determining that a prediction value is greater than a threshold value.

Clause 59: In some examples of any of clauses 1-58, the processing circuitry is configured to identify the at least one fourth portion at least in part by determining that the at least one fourth portion of the signal does not satisfy a first non-bypass condition and determining that the at least one fourth portion of the signal does not satisfy a second non-bypass condition.

Clause 60: In some examples of any of clauses 1-59, the processing circuitry is configured to determine the set of mean arterial pressure values at least in part by convolving a kernel and blood pressure values of the filtered signal and determining signal peaks based on convolving the kernel and the blood pressure values of the filtered signal.

Clause 61: In some examples of any of clauses 1-60, the processing circuitry is configured to convolve the kernel and the blood pressure values of the filtered signal at least in part by convolving a first kernel and the blood pressure values of the filtered signal to produce a first convolved signal. The processing circuitry is configured to determine the set of mean arterial pressure values at least in part by convolving a second kernel and the blood pressure values of the filtered signal and selecting one of the first convolved signal or the second convolved signal based on a power of the first convolved signal and a power of the second convolved signal. The processing circuitry is configured to determine the signal peaks at least in part by determining the signal peaks based on the selection of the first convolved signal or the second convolved signal.

Clause 62: In some examples, a method includes receiving, by processing circuitry, a signal indicative of a blood pressure of a patient and identifying, by processing circuitry, at least one first portion of the signal including a first characteristic of the signal exceeding a first threshold. The method also includes identifying, by processing circuitry, at least one first portion of the signal including a second characteristic of the signal exceeding a second threshold, the first characteristic being different than the second characteristic. The method further includes determining, by the processing circuitry, a filtered signal indicative of the blood pressure of the patient by excluding the at least one first portion and the at least one second portion from the signal. The method includes determining, by processing circuitry, a set of mean arterial pressure values based on the filtered signal and determining, by processing circuitry, an autoregulation status of the patient based on the set of mean arterial pressure values.

Clause 63: In some examples of clause 62, the first characteristic includes a blood pressure value.

Clause 64: In some examples of clause 62 or clause 63, identifying the at least one first portion of the signal includes determining that the first characteristic is one of less than a minimum blood pressure value or greater than a maximum blood pressure value.

Clause 65: In some examples of any of clauses 62-64, determining that the first characteristic is less than the minimum blood pressure value includes determining that the blood pressure value of the patient is less than twenty millimeters of mercury.

Clause 66: In some examples of any of clauses 62-65, the minimum blood pressure value is less than or equal to twenty-five millimeters of mercury.

Clause 67: In some examples of any of clauses 62-66, determining that the first characteristic is greater than the maximum blood pressure value includes determining that the blood pressure value is greater than two hundred and fifty millimeters of mercury.

Clause 68: In some examples of any of clauses 62-67, the maximum blood pressure value is greater than or equal to two hundred millimeters of mercury.

Clause 69: In some examples of any of clauses 62-68, identifying the at least one first portion of the signal includes determining that a difference in blood pressure between two consecutive portions of the signal is greater than a blood pressure variation value.

Clause 70: In some examples of any of clauses 62-69, determining that the difference in blood pressure between the two consecutive portions is greater than the blood pressure variation value includes determining that the difference in blood pressure between the two consecutive portions is greater than fifty millimeters of mercury.

Clause 71: In some examples of any of clauses 62-70, the blood pressure variation value is greater than or equal to forty millimeters of mercury.

Clause 72: In some examples of any of clauses 62-71, identifying the at least one first portion of the signal includes determining that a derivative of the signal exceeds a threshold rate for longer than a threshold time duration for a total change in the signal greater than a blood pressure variation value.

Clause 73: In some examples of any of clauses 62-72, determining that the derivative of the at least one first portion of the signal exceeds the threshold rate for longer than the threshold time duration for a total change greater than the blood pressure variation value includes determining that the derivative of the at least one first portion of the signal is greater than negative ten millimeters of mercury per second for longer than the threshold time duration for the total change greater than the blood pressure variation value.

Clause 74: In some examples of any of clauses 62-73, the threshold rate is greater than or equal to negative fifteen millimeters of mercury per second.

Clause 75: In some examples of any of clauses 62-74, determining that the derivative of the at least one first portion of the signal exceeds the threshold rate for longer than the threshold time duration for a total change greater than the blood pressure variation value includes determining that the derivative of the at least one first portion of the signal is less than positive ten millimeters of mercury per second for longer than the threshold time duration for the total change greater than the blood pressure variation value.

Clause 76: In some examples of any of clauses 62-75, the threshold rate is less than or equal to positive fifteen millimeters of mercury per second.

Clause 77: In some examples of any of clauses 62-76, determining that the derivative of the at least one first portion of the signal exceeds the threshold rate for longer than the threshold time duration for a total change greater than the blood pressure variation value includes determining that the derivative of the at least one first portion of the signal exceeds the threshold rate for longer than one second for the total change greater than the blood pressure variation value.

Clause 78: In some examples of any of clauses 62-77, the threshold time duration is greater than or equal to five hundred milliseconds.

Clause 79: In some examples of any of clauses 62-78, determining that the derivative of the at least one first portion of the signal exceeds the threshold rate for longer than the threshold time duration for a total change greater than the blood pressure variation value includes determining that the derivative of the at least one first portion of the signal exceeds the threshold rate for longer than the threshold time duration for the total change greater than twenty millimeters of mercury.

Clause 80: In some examples of any of clauses 62-79, the blood pressure variation value is greater than or equal to fifteen millimeters of mercury.

Clause 81: In some examples of any of clauses 62-80, identifying the at least one first portion of the signal includes determining that a number of consecutive samples of the blood pressure of the patient are within a predetermined range of deviation.

Clause 82: In some examples of any of clauses 62-81, determining that the number of consecutive samples are within the predetermined range of variation includes determining that five consecutive samples are within a range of variation of one millimeter of mercury.

Clause 83: In some examples of any of clauses 62-82, the predetermined range of variation is less than or equal to two millimeters of mercury.

Clause 84: In some examples of any of clauses 62-83, identifying the at least one first portion of the signal includes determining that a monotonic change in the blood pressure of the patient of the signal is greater than a blood pressure variation value.

Clause 85: In some examples of any of clauses 62-84, determining that the monotonic change is greater than a blood pressure variation value includes determining that the monotonic change is greater than one hundred and sixty millimeters of mercury.

Clause 86: In some examples of any of clauses 62-85, the blood pressure variation value is greater than or equal to one hundred and forty millimeters of mercury.

Clause 87: In some examples of any of clauses 62-86, identifying the at least one first portion includes determining that the monotonic change occurs for more than one second.

Clause 88: In some examples of any of clauses 62-87, identifying the at least one first portion includes determining that the monotonic change occurs for more than a threshold time duration, where the threshold time duration is greater than or equal to eight hundred milliseconds.

Clause 89: In some examples of any of clauses 62-88, identifying the at least one first portion of the signal includes determining that a level of noise of the signal is greater than the first threshold level.

Clause 90: In some examples of any of clauses 62-89, determining that the level of noise of the signal is greater than the first threshold level includes determining that a standard deviation of a derivative of the signal is greater than fifteen millimeters of mercury per second.

Clause 91: In some examples of any of clauses 62-90, determining that the level of noise of the signal is greater than the first threshold level includes determining that a standard deviation of a derivative of the signal is greater than a threshold rate, where the threshold rate is greater than or equal to twelve millimeters of mercury per second.

Clause 92: In some examples of any of clauses 62-91, identifying the at least one first portion of the signal includes determining that a diastolic value of the signal is greater than a blood pressure threshold value.

Clause 93: In some examples of any of clauses 62-92, determining that the diastolic value is greater than the blood pressure threshold value includes determining that the diastolic value of the signal is greater than one hundred and thirty millimeters of mercury.

Clause 94: In some examples of any of clauses 62-93, the blood pressure threshold value is greater than or equal to one hundred and twenty millimeters of mercury.

Clause 95: In some examples of any of clauses 62-94, determining that the diastolic value within the first portion is greater than the blood pressure threshold value includes determining that a percentile value is greater than the blood pressure threshold value.

Clause 96: In some examples of any of clauses 62-95, the percentile value is a tenth percentile of the signal.

Clause 97: In some examples of any of clauses 62-96, the percentile value is less than or equal to a fifteenth percentile of the signal.

Clause 98: In some examples of any of clauses 62-97, identifying the at least one first portion includes determining that a diastolic value of the signal is greater than a blood pressure threshold value for a threshold time duration.

Clause 99: In some examples of any of clauses 62-98, the threshold time duration is less than or equal to two seconds.

Clause 100: In some examples of any of clauses 62-99, further including identifying at least one third portion of the signal including a third characteristic of the signal exceeding a third threshold.

Clause 101: In some examples of any of clauses 62-100, determining the filtered signal includes modifying the at least one third portion of the signal.

Clause 102: In some examples of any of clauses 62-101, identifying the at least one third portion includes determining that a difference in blood pressure between a first consecutive portion of the signal and a second consecutive portion of the signal is greater than a first blood pressure variation value and determining that a difference in blood pressure between the second consecutive portion of the signal and a third consecutive portion of the signal is greater than a second blood pressure variation value.

Clause 103: In some examples of any of clauses 62-102, determining that the first sample is greater than the second sample by at least the first blood pressure threshold value includes determining that the first sample is greater than the second sample by at least twenty millimeters of mercury, and determining that the second sample is greater than the third sample by at least the second blood pressure threshold value includes determining that the second sample is greater than the third sample by at least twenty millimeters of mercury.

Clause 104: In some examples of any of clauses 62-103, modifying the at least one third portion of the signal includes setting the second consecutive portion of the signal to a modified value. A difference between the modified value and a value the first consecutive portion of the signal is less than a difference between the modified value and a value the second consecutive portion of the signal. A difference between the modified value and a value the third consecutive portion of the signal is less than the difference between the modified value and the value the second consecutive portion of the signal.

Clause 105: In some examples of any of clauses 62-104, modifying the at least one third portion of the signal includes setting the second consecutive portion of the signal to a mean or a median of a value the first consecutive portion of the signal and a value the third consecutive portion of the signal.

Clause 106: In some examples of any of clauses 62-105, identifying the at least one third portion includes determining a low-pass-filtered signal from the at least one third portion of the signal and determining that a difference between a blood pressure value of the at least one third portion of the signal and an associated blood pressure value of low-pass-filtered signal is greater than a blood pressure variation value.

Clause 107: In some examples of any of clauses 62-106, determining the low-pass-filtered signal includes low-pass filtering the signal using a cutoff frequency of between approximately ten hertz and approximately thirty hertz.

Clause 108: In some examples of any of clauses 62-107, determining that the difference between the blood pressure value of the at least one third portion of the signal and the associated blood pressure value is greater than the blood pressure variation value includes determining that the difference between the blood pressure value of the at least one third portion of the signal and the associated blood pressure value is greater than three millimeters of mercury.

Clause 109: In some examples of any of clauses 62-108, the blood pressure variation value is greater than or equal to two millimeters of mercury.

Clause 110: In some examples of any of clauses 62-109, identifying the at least one third portion includes determining that the signal has an invalid value within the at least one third portion for less than a threshold time duration.

Clause 111: In some examples of any of clauses 62-110, the threshold time duration is less than or equal to one second.

Clause 112: In some examples of any of clauses 62-111, identifying the at least one third portion includes determining that the third characteristic of the signal exceeds the third threshold for less than a threshold time duration.

Clause 113: In some examples of any of clauses 62-112, the threshold time duration is less than or equal to one second.

Clause 114: In some examples of any of clauses 62-113, identifying at least one fourth portion of the signal including a fourth characteristic of the signal indicates that the patient is undergoing a cardiopulmonary bypass procedure. In addition, determining a subset of the set of mean arterial pressure values for the at least one fourth portion based on a moving average of the signal is in response to determining that the fourth characteristic of the signal indicates that the patient is undergoing the cardiopulmonary bypass procedure.

Clause 115: In some examples of any of clauses 62-114, identifying the at least one fourth portion includes determining that a mean power of the signal is less than a threshold power level.

Clause 116: In some examples of any of clauses 62-115, identifying the at least one fourth portion includes determining that a diastolic value of the signal is less than a blood pressure threshold value.

Clause 117: In some examples of any of clauses 62-116, determining that the diastolic value is less than the blood pressure threshold value includes determining that a percentile value is less than the blood pressure threshold value, where the percentile value is less than or equal to a fifteenth percentile of the signal.

Clause 118: In some examples of any of clauses 62-117, identifying the at least one fourth portion includes determining that a total power within a frequency band is less than a threshold power level, the frequency band including an estimated heart rate frequency of the patient.

Clause 119: In some examples of any of clauses 62-118, identifying the at least one fourth portion includes determining that a prediction value is greater than a threshold value.

Clause 120: In some examples of any of clauses 62-119, identifying the at least one fourth portion includes determining that the at least one fourth portion of the signal does not satisfy a first non-bypass condition and determining that the at least one fourth portion of the signal does not satisfy a second non-bypass condition.

Clause 121: In some examples of any of clauses 62-120, determining the set of mean arterial pressure values includes convolving a kernel and blood pressure values of the filtered signal and determining signal peaks based on convolving the kernel and the blood pressure values of the filtered signal.

Clause 122: In some examples of any of clauses 62-121, convolving the kernel and the blood pressure values of the filtered signal includes convolving a first kernel and the blood pressure values of the filtered signal to produce a first convolved signal. Determining the set of mean arterial pressure values includes convolving a second kernel and the blood pressure values of the filtered signal and selecting one of the first convolved signal or the second convolved signal based on a power of the first convolved signal and a power of the second convolved signal. Determining the signal peaks includes determining the signal peaks based on the selection of the first convolved signal or the second convolved signal.

Clause 123: In some examples, a device includes a display, sensing circuitry configured to generate a signal indicative of the blood pressure of the patient, and a memory configured to store a first threshold for a first characteristic of the signal and a second threshold for a second characteristic of the signal. The device also includes processing circuitry configured to identify at least one first portion of the signal including the first characteristic of the signal exceeding the first threshold. The processing circuitry is also configured to identify at least one second portion of the signal including the second characteristic of the signal exceeding the second threshold, the first characteristic being different than the second characteristic. The processing circuitry is further configured to determine a filtered signal indicative of the blood pressure of the patient by excluding the at least one first portion and the at least one second portion from the signal. The processing circuitry is configured to determine a set of mean arterial pressure values based on the filtered signal and determine an autoregulation status of the patient based on the set of mean arterial pressure values.

Clause 124: In some examples of clause 123, the processing circuitry is configured to perform the method of clauses 62-122 or any combination thereof.

Clause 125: In some examples, a device includes a computer-readable medium having executable instructions stored thereon, configured to be executable by processing circuitry for causing the processing circuitry to receive a signal indicative of a blood pressure of the patient and identify at least one first portion of the signal including a first characteristic of the signal exceeding a first threshold. The instructions further cause the processing circuitry to identify at least one second portion of the signal including a second characteristic of the signal exceeding a second threshold, the first characteristic being different than the second characteristic. The instructions also cause the processing circuitry to determine a filtered signal indicative of the blood pressure of the patient by excluding the at least one first portion and the at least one second portion from the signal. The instructions also cause the processing circuitry to determine a set of mean arterial pressure values based on the filtered signal and determine an autoregulation status of the patient based on the set of mean arterial pressure values.

Clause 126: In some examples of clause 125, the instructions further cause the processing circuitry to perform the method of clauses 62-122 or any combination thereof.

Clause 127: In some examples, a method includes receiving, by processing circuitry, a signal indicative of a blood pressure of a patient and identifying, by processing circuitry, at least one first portion of the signal including a first characteristic of the signal exceeding a first threshold. The method also includes identifying, by processing circuitry, at least one first portion of the signal including a second characteristic of the signal exceeding a second threshold, the first characteristic being different than the second characteristic. The method further includes determining, by the processing circuitry, a filtered signal indicative of the blood pressure of the patient by modifying the at least one first portion and the at least one second portion from the signal. The method includes determining, by processing circuitry, a set of mean arterial pressure values based on the filtered signal and determining, by processing circuitry, an autoregulation status of the patient based on the set of mean arterial pressure values.

Clause 128: In some examples, a device includes processing circuitry configured to perform the method of clause 62-122 or any combination thereof.

Clause 129: In some examples, a method includes receiving, by processing circuitry, a signal indicative of a blood pressure of a patient and identifying, by processing circuitry, at least one portion of the signal including a characteristic of the signal indicating that the patient is undergoing a cardiopulmonary bypass procedure. The method further includes determining, by the processing circuitry, a set of mean arterial pressure values based on the signal and determining, by processing circuitry, a subset of the set of mean arterial pressure values for the at least one portion of the signal based on a moving average of the signal in response to determining that the characteristic of the signal indicates that the patient is undergoing the cardiopulmonary bypass procedure. The method includes determining, by processing circuitry, an autoregulation status of the patient based on the set of mean arterial pressure values and the subset of the set of mean arterial pressure values for the at least one portion of the signal.

Clause 130: In some examples, a device includes processing circuitry configured to perform the method of clause 62-122 or any combination thereof.

Clause 131: In some examples, a method includes receiving, by processing circuitry, a signal indicative of a blood pressure of a patient and convolving, by processing circuitry, a kernel and blood pressure values of the signal. The method also includes determining, by processing circuitry, signal peaks based on convolving the kernel and the blood pressure values of the signal. The method further includes determining, by the processing circuitry, a set of mean arterial pressure values based on the blood pressure values of the signal and the signal peaks. The method includes determining, by processing circuitry, an autoregulation status of the patient based on the set of mean arterial pressure values.

Clause 132: In some examples, a device includes processing circuitry configured to perform the method of clause 62-122 or any combination thereof.

Clause 133: In some examples, a device includes means for receiving a signal indicative of a blood pressure of the patient and means for identifying at least one first portion of the signal including a first characteristic of the signal exceeding a first threshold. The device also includes means for identifying at least one second portion of the signal including a second characteristic of the signal exceeding a second threshold, the first characteristic being different than the second characteristic. The device includes means for determining a filtered signal indicative of the blood pressure of the patient by excluding the at least one first portion and the at least one second portion from the signal. The device further includes means for determining a set of mean arterial pressure values based on the filtered signal and means for determining an autoregulation status of the patient based on the set of mean arterial pressure values.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150-152 and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210, 214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

In examples in which processing circuitry 110 is described herein as determining that a value is less than or equal to another value, this description may also include processing circuitry 110 determining that a value is only less than the other value. Similarly, in examples in which processing circuitry 110 is described herein as determining that a value is less than another value, this description may also include processing circuitry 110 determining that a value is less than or equal to the other value. The same properties may also apply to the terms "greater than" and "greater than or equal to."

Various examples of the disclosure have been described. Any combination of the described systems, operations, or functions is contemplated. These and other examples are within the scope of the following claims.

What is claimed is:

1. A device comprising:
    processing circuitry configured to:
        receive a signal indicative of a blood pressure of a patient;
        identify at least one first portion of the signal comprising a first characteristic of the signal exceeding a first threshold;
        identify at least one second portion of the signal comprising a second characteristic of the signal exceeding a second threshold, the first characteristic being different than the second characteristic;
        determine a filtered signal indicative of the blood pressure of the patient by excluding the at least one first portion and the at least one second portion from the signal;
        determine a set of mean arterial pressure values based on the filtered signal; and
        determine an autoregulation status of the patient based on the set of mean arterial pressure values.

2. The device of claim 1,
    wherein the first characteristic comprises a blood pressure value, and
    wherein the processing circuitry is configured to identify the at least one first portion of the signal at least in part by determining that the first characteristic is one of less than a minimum blood pressure value or greater than a maximum blood pressure value.

3. The device of claim 1, wherein the processing circuitry is configured to identify the at least one first portion of the signal at least in part by determining that a difference in blood pressure between two consecutive portions of the signal is greater than a blood pressure variation value.

4. The device of claim 1, wherein the processing circuitry is configured to identify the at least one first portion of the signal at least in part by determining that a derivative of the signal exceeds a threshold rate for longer than a threshold time duration for a total change in the signal greater than a blood pressure variation value.

5. The device of claim 1, wherein the processing circuitry is configured to identify the at least one first portion of the signal at least in part by determining that a number of consecutive samples of the blood pressure of the patient are within a predetermined range of deviation.

6. The device of claim 1, wherein the processing circuitry is configured to identify the at least one first portion of the signal at least in part by determining that a monotonic change in the blood pressure of the patient of the signal is greater than a blood pressure variation value.

7. The device of claim 1, wherein the processing circuitry is configured to identify the at least one first portion of the signal at least in part by determining that a level of noise of the signal is greater than the first threshold level.

8. The device of claim 1, wherein the processing circuitry is configured to identify the at least one first portion of the signal at least in part by determining that a diastolic value of the signal is greater than a blood pressure threshold value.

9. The device of claim 1,
wherein the processing circuitry is further configured to identify at least one third portion of the signal comprising a third characteristic of the signal exceeding a third threshold, and
wherein the processing circuitry is configured to determine the filtered signal at least in part by modifying the at least one third portion of the signal.

10. The device of claim 9, wherein the processing circuitry is configured to identify the at least one third portion of the signal at least in part by:
determining that a difference in blood pressure between a first consecutive portion of the signal and a second consecutive portion of the signal is greater than a first blood pressure variation value; and
determining that a difference in blood pressure between the second consecutive portion of the signal and a third consecutive portion of the signal is greater than a second blood pressure variation value,
wherein the processing circuitry is configured to modify the at least one third portion of the signal at least in part by setting the second consecutive portion of the signal to a modified value closer to the first and third consecutive portions of the signal than to an unmodified value of the second consecutive portion of the signal.

11. The device of claim 1, wherein the processing circuitry is further configured to:
identify at least one fourth portion of the signal comprising a fourth characteristic of the signal indicating that the patient is undergoing a cardiopulmonary bypass procedure; and
determine a subset of the set of mean arterial pressure values for the at least one fourth portion based on a moving average of the signal in response to determining that the fourth characteristic of the signal indicates that the patient is undergoing the cardiopulmonary bypass procedure.

12. The device of claim 11, wherein the processing circuitry is configured to identify the at least one fourth portion at least in part by determining that a total power within a frequency band is less than a threshold power level, the frequency band including an estimated heart rate frequency of the patient.

13. The device of claim 1, wherein the processing circuitry is configured to determine the set of mean arterial pressure values at least in part by:
convolving a kernel and blood pressure values of the filtered signal; and
determining signal peaks based on convolving the kernel and the blood pressure values of the filtered signal.

14. The device of claim 13,
wherein the processing circuitry is configured to convolve the kernel and the blood pressure values of the filtered signal at least in part by convolving a first kernel and the blood pressure values of the filtered signal to produce a first convolved signal,
wherein the processing circuitry is configured to determine the set of mean arterial pressure values at least in part by:
convolving a second kernel and the blood pressure values of the filtered signal; and
selecting one of the first convolved signal or the second convolved signal based on a power of the first convolved signal and a power of the second convolved signal, and
wherein the processing circuitry is configured to determine the signal peaks at least in part by determining the signal peaks based on the selection of the first convolved signal or the second convolved signal.

15. A method comprising:
receiving, by processing circuitry, a signal indicative of a blood pressure of a patient;
identifying, by the processing circuitry, at least one first portion of the signal comprising a first characteristic of the signal exceeding a first threshold;
identifying, by the processing circuitry, at least one second portion of the signal comprising a second characteristic of the signal exceeding a second threshold, the first characteristic being different than the second characteristic;
determining, by the processing circuitry, a filtered signal indicative of the blood pressure of the patient by excluding the at least one first portion and the at least one second portion from the signal;
determining, by the processing circuitry, a set of mean arterial pressure values based on the filtered signal; and
determining, by the processing circuitry, an autoregulation status of the patient based on the set of mean arterial pressure values.

16. The method of claim 15, further comprising identifying, by the processing circuitry, at least one third portion of the signal comprising a third characteristic of the signal exceeding a third threshold,
wherein determining the filtered signal comprises modifying the at least one third portion of the signal.

17. The method of claim 15, further comprising:
identifying, by the processing circuitry, at least one fourth portion of the signal comprising a fourth characteristic of the signal indicating that the patient is undergoing a cardiopulmonary bypass procedure; and
determining, by the processing circuitry, a subset of the set of mean arterial pressure values for the at least one fourth portion based on a moving average of the signal in response to determining that the fourth characteristic of the signal indicates that the patient is undergoing the cardiopulmonary bypass procedure.

18. A device comprising a non-transitory computer-readable medium having executable instructions stored thereon, configured to be executable by processing circuitry for causing the processing circuitry to:

receive a signal indicative of a blood pressure of a patient;

identify at least one first portion of the signal comprising a first characteristic of the signal exceeding a first threshold;

identify at least one second portion of the signal comprising a second characteristic of the signal exceeding a second threshold;

determine a filtered signal indicative of the blood pressure of the patient by excluding the at least one first portion and the at least one second portion from the signal;

determine a set of mean arterial pressure values based on the filtered signal; and determine an autoregulation status of the patient based on the set of mean arterial pressure values.

19. The device of claim 18, wherein the instructions are further configured to cause the processing circuitry to identify at least one third portion of the signal comprising a third characteristic of the signal exceeding a third threshold, and wherein the instructions to determine the filtered signal comprise instructions to modify the at least one third portion of the signal.

20. The device of claim 18, wherein the instructions are further configured to cause the processing circuitry to:

identify at least one fourth portion of the signal comprising a fourth characteristic of the signal indicating that the patient is undergoing a cardiopulmonary bypass procedure; and determine a subset of the set of mean arterial pressure values for the at least one fourth portion based on a moving average of the signal in response to determining that the fourth characteristic of the signal indicates that the patient is undergoing the cardiopulmonary bypass procedure.

\* \* \* \* \*